United States Patent
Ciccognani et al.

(10) Patent No.: US 9,610,350 B2
(45) Date of Patent: Apr. 4, 2017

(54) BROAD SPECTRUM PRESERVATION BLENDS

(75) Inventors: Diana T. Ciccognani, Cheshire, CT (US); Kevin N. DiNicola, Wolcott, CT (US); Katherine P. Roberts, Derby, CT (US); Laura M. Szymczak, Tinton Falls, NJ (US)

(73) Assignee: Arch Personal Care Products, L.P., South Plainfield, NJ (US)

( * ) Notice: Subject to any disclaimer, the term of this patent is extended or adjusted under 35 U.S.C. 154(b) by 769 days.

(21) Appl. No.: 12/856,867

(22) Filed: Aug. 16, 2010

(65) Prior Publication Data

US 2011/0086918 A1 Apr. 14, 2011

Related U.S. Application Data

(60) Provisional application No. 61/234,456, filed on Aug. 17, 2009.

(51) Int. Cl.
| | | |
|---|---|---|
| *A01N 37/06* | (2006.01) | |
| *A01P 1/00* | (2006.01) | |
| *A61K 47/12* | (2006.01) | |
| *A61K 8/34* | (2006.01) | |
| *A61K 8/36* | (2006.01) | |
| *A61K 8/368* | (2006.01) | |
| *A61K 9/00* | (2006.01) | |
| *A61K 9/08* | (2006.01) | |
| *A61K 9/107* | (2006.01) | |
| *A61K 47/10* | (2017.01) | |
| *A61Q 5/02* | (2006.01) | |
| *A61Q 19/00* | (2006.01) | |

(52) U.S. Cl.
CPC .............. *A61K 47/12* (2013.01); *A61K 8/345* (2013.01); *A61K 8/36* (2013.01); *A61K 8/368* (2013.01); *A61K 9/0014* (2013.01); *A61K 9/08* (2013.01); *A61K 9/107* (2013.01); *A61K 47/10* (2013.01); *A61Q 5/02* (2013.01); *A61Q 19/00* (2013.01)

(58) Field of Classification Search
CPC ........ A61K 47/10; A61K 47/12; A61K 8/345; A61K 8/36; A61K 8/368; A61K 9/0014; A61K 9/08; A61K 9/107; A61Q 19/00; A61Q 5/02

USPC ........................................................ 514/557
See application file for complete search history.

(56) References Cited

U.S. PATENT DOCUMENTS

| | | | | |
|---|---|---|---|---|
| 5,670,160 | A | * | 9/1997 | Eggensperger et al. ...... 424/405 |
| 2008/0312195 | A1 | * | 12/2008 | Simsch et al. ................ 514/159 |
| 2009/0035243 | A1 | * | 2/2009 | Czarnota et al. .............. 424/64 |
| 2009/0123577 | A1 | | 5/2009 | Beilfuss et al. |

FOREIGN PATENT DOCUMENTS

WO WO 02089759 11/2002

OTHER PUBLICATIONS

Rosen et al.,J. Soc. Cosmet. Chem., 24, 663-675 ,Sep. 16, 1973.*
EP 10810452.2 Search Report and Opinion, Completed Sep. 6, 2013.
"Cosgard, conservant cosmetic agreat Ecocert-Mayam", 2005, Retrieved from the Internet: http://www.pcfarm.ro/produs/6748/Cosgard,-conservant-cosmetic-agrent-Ecocert--Mayam.
"Geogard ECT (was Mikrokill ECT)", 2010, Retrieved from the Internet: http://www.cosmeticingredients.co.uk/products.asp?prod=1209.
"Mikrokill® ECT", Arch Personal Care Products, L.P., Jan. 29, 2010, pp. 1-8, Retrieved from the Internet: http://az290931.vo.msecnd.net/www.in-cosmetics.com/_novadocuments/2198x$query$xvx$eq$x634484823552730000 or http://www.in-cosmetics.com/_novadocuments/4484.
Adina cosmetic ingredients, Nov. 2009 (Nov. 2009), Retrieved from the Internet: http://www.cosmeticingredients.co.uk/news_a.asp?story=67.
"Arch's Microkill ECT lives up to Cosmos and Ecocert expectations", Cosmetics International, Cosmetics Communications, London, GB, Dec. 11, 2009 (Dec. 11, 2009), p. 13, XP001526505, ISSN: 0963-6137.
"MSDS Mikrokill ECT", www.sinthaichem.com, Nov. 29, 2009, pp. 1-11, Retrieved from the Internet: http://www.sinthaichem.com/2011/attachments/download/99/Mikrokill%20ECT%20(139650)%20-%20MSDS.pdf.

* cited by examiner

*Primary Examiner* — Johann R Richter
*Assistant Examiner* — Courtney Brown
(74) *Attorney, Agent, or Firm* — Dority & Manning, P.A.

(57) ABSTRACT

A composition having effective broad spectrum preservation activity comprising benzyl alcohol, salicylic acid, sorbic acid and a compound selected from the group consisting of 1,3-propanediol, glycerin and combinations thereof.

22 Claims, No Drawings

BROAD SPECTRUM PRESERVATION BLENDS

CROSS REFERENCE TO RELATED APPLICATIONS

This application claims the benefit of U.S. Provisional Patent Application Ser. No. 61/234,456, filed on Aug. 17, 2009, the disclosure of which is incorporated herein by reference in its entirety.

BACKGROUND OF THE INVENTION

Field of the Invention

The present invention relates to broad spectrum preservation blends. In particular, the present invention relates to preservation blends that incorporate benzyl alcohol, salicylic acid, sorbic acid and an additive. The additive is selected from the group consisting of 1,3-propanol, dehydroacetic acid, glycerin and a combination thereof. The preservation blends of the invention are stable at low temperatures and have a high efficacy against a broad spectrum of microorganisms at a wider than expected pH range.

Brief Description of Art

Preservatives have wide applications in fields like personal care, industrial, health and hygiene, pharmaceutical and wood protection. Preservatives can be a single agent or a blend of multiple agents.

Ideally, a preservative has broad-spectrum activity against all types of microorganisms at various pH levels. The preservative should also have high efficacy so that a minimum amount of the preservative can be used to save cost and to avoid or reduce any possible adverse effects caused by the preservative. Also, it is desirable that the preservative is stable to any changes in temperature encountered during manufacturing, packaging, and shipping as well as during storage of the preservative. Further, an ideal preservative is physically and chemically compatible with ingredients of different application systems so that one preservative can suitably be incorporated in various products.

Benzyl alcohol, salicylic acid and sorbic acid are known preservative agents, but individually they are of limited usefulness with regards to broad spectrum activity because these actives are known to have poor activity at more neutral and alkaline pH. In addition, salicylic acid and sorbic acid can be difficult to solubilize at high concentrations, thus making an effective concentrate difficult to achieve.

Certain preservative blends containing either one or more of benzyl alcohol, salicylic acid, or sorbic acid are known. For example, Optiphen® BSB-N from ISP is a combination of benzoic acid, sorbic acid and benzyl alcohol and glycerin. Sharomix® 705 from Sharon Laboratories is a liquid blend of benzyl alcohol, benzoic acid, sorbic acid and dehydroacetic acid. However, the application of these preservatives is limited because they are only suitable for low pH systems (up to pH 6.5).

US patent application publication 2009/0123577 to Air Liquide Sante, the disclosure of which is incorporated herein in its entirety, discloses a liquid concentrate for preserving cosmetics including a carboxylic acid component (A) containing at least two carboxylic acids selected from benzoic acid, propionic acid, salicylic acid, sorbic acid, 4-hydroxybenzoic acid, dehydroacetic acid, formic acid and 10-undecylenic acid; an alcohol component (B) selected from phenoxyethanol, benzyl alcohol. Unfortunately, the preservative concentrate disclosed in the publication uses up to 40% of water as solvent. As water freezes at 0° C., this may cause difficulties in handling the disclosed concentrate at low temperatures. Further, the disclosed preservatives are suitable for use in systems having a pH of less than 7, in particular less than 6.

Accordingly, there is a continuing need for another preservative, which is stable at low temperatures, and which has a high efficacy against a broad spectrum of microorganisms at a wide pH range. The present invention provides one answer to that need.

BRIEF SUMMARY OF THE INVENTION

One aspect of the present invention is directed to a composition having effective broad spectrum preservation activity comprising (a) benzyl alcohol, (b) salicylic acid, (c) sorbic acid and (d) a compound selected from the group consisting of 1,3-propanediol, glycerin and a combination thereof. In the composition, component (a) is present at a concentration of from about 70% to about 90% by weight, component (b) is present at a concentration of from about 1% to 15% by weight, component (c) is present at a concentration of from about 1% to 4% by weight, and component (d) is present at a concentration of from about 1% to 15% by weight, provided that the total amount of components (b) and (c) is no more than 15% by weight, all based on the total weight of the composition. The composition may optionally contain dehydroacetic acid.

Still another aspect of the present invention is directed to a composition having effective broad spectrum preservation activity comprising benzyl alcohol, salicylic acid, sorbic acid, and glycerin wherein benzyl alcohol is present at a concentration of from about 77% to about 86%, salicylic acid is present at a concentration of from about 8% to about 11%, sorbic acid is present at a concentration of from about 2.5% to about 3.5% and glycerin is present at a concentration of from about 3% to about 5% by weight, based on the total weight of the composition.

Yet another aspect of the present invention is directed to topical formulations containing the preservative of the invention.

DETAILED DESCRIPTION OF THE INVENTION

The present invention provides a stable preservation blend composition having effective broad spectrum preservation activity at neutral, acidic and alkaline pH. The composition contains: (a) benzyl alcohol, (b) salicylic acid, (c) sorbic acid, and (d) a compound selected from the group consisting of 1,3-propanediol, glycerin and a combination thereof.

The amount of components (a)-(d) of the preservation blend according to this invention may vary. Preferably, benzyl alcohol constitutes from about 70% to about 90% by weight, more preferably, about 77% to about 86% by weight, based on the total weight of the composition. Salicylic acid is present at a concentration of from about 1% to about 15%, preferably from about 3% to 12%, more preferably from 8% to 11%; sorbic acid is present at a concentration of from about 1% to about 4%, preferably from 2.5% to about 3.5% by weight, and component (d) is present at a concentration of from 1% to 15%, preferably from 1% to 10% by weight, more preferably from 2% to 5%, based on the total weight of the composition. Preferably, the total amount of components (b) and (c) is no more than 15% by weight based on the total weight of the composition. In some embodiments, the total weight percentages of components (a), (b), (c) and (d) combined is 100%.

Optionally, the preservation blend of the invention may additionally contain dehydroacetic acid. If present, the total amount of salicylic acid, sorbic acid, and dehydroacetic acid is no more than 15 wt % based on the total weight of the preservation blend. In one embodiment, the weight ratio of dehydroacetic acid to component (d) of the preservation blend is from about 3:1 to about 1:1.

In some embodiments of the invention, the preservation blends are free or substantially free of water. In other embodiments, the blends are free or substantially free of benzoic acid. As used herein, "essentially free" is intended to mean that the composition preferably contains less than 1000 ppms, more preferably less than 100 ppms, and most preferably zero ppms, of water or benzoic acid.

In one preferred embodiment, the invention provides a preservation blend composition comprising from about 77 wt % to about 86 wt % of benzyl alcohol, from about 8 wt % to about 11 wt % of salicylic acid, from about 2.5 wt % to about 3.5 wt % of sorbic acid and from about 2 wt % to about 5 wt % of glycerin by weight, based on the total weight of the composition.

As used herein, the term "effective preservation activity" means that its activity is such that the composition or formulation is protected for a sustained period of time, in particular during the so-called "shelf life" of the product. The "shelf-life" of a product is determined according to methods generally known in the art.

The term "broad spectrum" as used in this specification and claims means a preservative having good preservation properties against a wide spectrum of microorganisms that commonly will cause deterioration or spoilage of personal care products, such as cosmetics, and various products with other applications such as pharmaceutical compositions, wood preservative systems, industrial, and health and hygiene.

The preservation blends of the invention have a relatively high organic acid level, yet are stable at low temperatures. They are effective at low concentrations and have a broad-spectrum of activity against various types of microorganisms. The preservative blends of the invention also have surprisingly good antimicrobial performance at neutral, acidic and low alkaline pH, and can be incorporated into a wide range of formulations.

The composition of the present invention can be made by mixing benzyl alcohol, salicylic acid, sorbic acid and component (d) in any order. It can be suitably incorporated into various products, for example, personal care formulations, pharmaceutical compositions, wood preservative systems, industrial, and health and hygiene products.

In one embodiment, this invention further relates to topical formulations containing a preservation blend as defined herein. Preferably, the preservation blend is present at a concentration of from about 0.5% to about 1.5%, more preferably from about 0.6% to about 1% based on the total weight of the topical formulation. Topical compositions comprise dermatological formulations (or topical pharmaceutical formulations), as well as cosmetic formulations. The topical formulations may further contain other ingredients or additives used in dermatological or in cosmetic formulations, including other active ingredients.

The formulations according to the present invention are formulated into forms that are useful in personal care products, especially in emulsions.

The topical formulations according to the present invention may additionally contain further ingredients or additives such as solvents, surfactants, emulsifiers, consistency factors, conditioners, emollients, skin caring ingredients, moisturizers, thickeners, lubricants, fillers, anti-oxidants, other preservatives, active ingredients, in particular dermatologically active ingredients, fragrances and the like, as well as mixtures thereof. Active ingredients as mentioned herein comprise, for example, anti-inflammatories, anti-bacterials, anti-fungals and the like agents. Active ingredients suited for topical applications are particularly preferred.

Suitable surfactants comprise: alkyl sulfates e.g. sodium lauryl sulfate, ammonium lauryl sulfate; sodium cetearyl sulfate; alkyl sulfoacetates e.g. sodium lauryl sulfoacetate; alkyl ether sulfates e.g. sodium laureth sulfate; sodium trideceth sulfate; sodium oleth sulfate; ammonium laureth sulfate; alkyl ether sulfosuccinates e.g. disodium laureth sulfosuccinate; alkyl glycosides e.g. decyl glucoside; lauryl glucoside; alkyl isethionates amphoterics e.g. cocamidopropyl betaine; sodium cocoamphoacetate; sodium lauroamphoacetate; disodium lauroamphodiacetate; disodium cocoamphodiacetate; sodium lauroamphopripionate; disodium lauroamphodipropionate; potassium or ammonium salts of the aforementioned amphoterics; capryl/capramidopropyl betaine; undecylenamidopropyl betaine; lauromidopropyl betaine; and fatty alcohol polyglycol ethers.

Suitable emulsifiers are e.g. anionics as salts of fatty acids e.g. sodium stearate or sodium palmitate, organic soaps e.g. mono-, di- or triethanolaminoeate, sulfated or sulfonated compounds e.g. sodium lauryl sulfate or sodium cetyl sulfonate, saponines, lamepones; cationics as quaternary ammonium salts; nonionics as fatty alcohols, fatty acid ester with saturated or unsaturated fatty acids, polyoxyethylenesters or polyoxyethylenethers of fatty acids, polymers from ethylene oxide and propylene oxide or propylene glycol, amphoterics as phosphatides, proteins as gelatine, casein alkylamidobetaines, alkyl betaines and amphoglycinates, alkyl phosphates, alkylpolyoxyethylene phoaphates or the corresponding acids, silicone derivatives, e.g. alkyl dimethiconecoplyol.

Suitable consistency factors are e.g. fatty alcohols or their mixtures with fatty acid esters, e.g. acetylated lanolin alcohol, aluminum stearates, carbomer, cetyl alcohol, glyceryl oleate, glyceryl stearate, glyceryl stearate (and) PEG 100 stearate, magnesium stearate, magnesium sulfate, oleic acid, stearic acid, stearyl alcohol, myristyl myristate, isopropyl palmitate, beeswax and synthetic equivalents thereof, carbomers, and the like. Suitable conditioners are e.g. alkylamido ammonium lactate, cetrimonium chloride and distearoylethyl hydroxyethylmonium methosulfate and cetearyl alcohol, cetyl dimethicone, cetyl ricinoleate, dimethicone, laureth-23, laureth-4, polydecene, retinyl palmitate, quaternized protein hydrolysates, quaternized cellulose and starch derivatives, quaternized copolymers of acrylic or methacrylic acid or salts, quaternized silicone derivatives.

Suitable emollients are e.g. cetearyl isononanoate, cetearyl octanoate, decyl oleate, isooctyl stearate, coco caprylate/caprate, ethylhexyl hydroxystearate, ethylhexyl isononanoate, isopropyl isostearate, isopropyl myristate, oleyl oleate, hexyl laurate, paraffinum liquidum, PEG-75 lanolin, PEG-7 glyceryl cocoate, petrolatum, ozokerite cyclomethicone, dimethicone, dimethicone copolyol, dicaprylyl ether, *butyrospermum parkii, buxus chinensis*, canola, *carnauba cera, copernicia cerifera, oenothera biennis, elaeis guineensis, prunus dulcis*, squalane, *zea mays, glycine soja, helianthus annuus*, lanolin, hydrogenated castor oil, hydrogenated coconut oil, hydrogenated polyisobutene, sucrose cocoate, stearoxy dimethicone, lanolin alcohol, isohexadecane.

Suitable skin care ingredients are e.g. plant extracts, bisabolol, anti-inflammatory agents, urea, allantoin, panthenol and panthenol derivatives, phytantriol, vitamins A, E, C, D, ceramides of animal or plant origin, lecithins, and the like.

Suitable moisturizers are e.g. butylenes glycol, cetyl alcohol, dimethicone, dimyristyl tartrate, glucose glycereth-26, glycerin, glyceryl stearate, hydrolyzed milk protein, lactic acid, lactose and other sugars, laureth-8, lecithin, octoxyglycerin, PEG-12, PEG 135, PEG-150, PEG-20, PEG-8, pentylene glycol, hexylene glycol, phytantriol, poly quaternium-39 PPG-20 methyl glucose ether, propylene glycol, sodium hyaluronate, sodium lactate, sodium PCA, sorbitol, succinoglycan, synthetic beeswax, tri-C14-15 alkyl citrate, starch.

Suitable thickeners are e.g. acrylates/steareth-20 methacrylate copolymer, carbomer, carboxymethyl starch, cera alba, dimethicone/vinyl dimethicone crosspolymer, propylene glycol alginate, hydroxyethylcellulose, hydroxypropyl methylcellulose, silica, silica dimethyl silylate, xanthan gum, hydrogenated butylenes/ethylene/styrene copolymer.

Suitable lubricants are e.g. adipic acid, fumaric acid and its salts, benzoic acid and its salts, glycerine triacetate, sodium or magnesium lauryl sulfate, magnesium stearate, solid polyethylenglycol, polyvinylpyrrolidone, boric acid, mono-laurate or mono-palmitate, myristyl alcohol, cetyl alcohol, cetylstearyl alcohol, talcum, calcium or magnesium salts of higher fatty acids, mono-, di- or triglycerides of higher fatty acids, polytetrafluorethylen.

Suitable antioxidants are e.g. sulfites, e.g. sodium sulfite, tocopherol or derivates thereof, ascorbic acid or derivates thereof, citric acid, propyl gallate, chitosan glycolate, cysteine, N-acetyl cysteine plus zinc sulfate, thiosulfates, e.g. sodium thiosulfate, polyphenoles and the like.

The compositions may further contain active ingredients, e.g. anti-microbials, anti-inflammatories, plant extracts, bisabolol, panthenol, tocopherol, actives for anti-stinging, anti-irritant or anti-dandruff applications, or anti-aging agents such as retinol, melibiose and the like. Other suitable actives are e.g. *Medicago officinalis, Actinidia chinensis*, allantoin, *Aloe barbadensis, Anona cherimolia, Anthemis nobilis, Arachis hypogaea, Arnica Montana, Avena sativa*, beta-carotene, bisabolol, *Borago officinalis*, butylenes glycol, *Calendula officinalis, Camellia sinensis*, camphor, *Candida bombicola*, capryloyl glycine, *Carica papaya, Centaurea cyanus*, cetylpyridinium chloride, *Chamomilla recutita, Chenopodium quinoa, Chinchona succirubra, Chondrus crispus, Citrus aurantium dulcis, Citrus grandis, Citrus limonum, Cocos nucifera, Coffea Arabica, Crataegus monogina, Cucumis melo*, dichlorophenyl imidazoldioxolan, *Enteromorpha compressa, Equisetum arvense*, ethoxydiglycol, ethyl panthenol, farnesol, ferulic acid, *Fragaria chiloensis, Gentiana lutea, Ginkgo biloba*, glycerin, glyceryl laurate, *Glycyrrhiza glabra, Hamamelis virginiana*, heliotropine, hydrogenated palm glycerides, citrates, hydrolyzed castor oil, hydrolyzed wheat protein, *Hypericum perforatum, Iris florentina, Juniperus communis, Lactis proteinum*, lactose, *Lawsonia inermis*, linalool, *Linum usitatissimum*, lysine, magnesium aspartate, *Magnifera indica, Malva sylvestris*, mannitol, mel *Melaleuca alternifolia, Mentha piperita*, menthol, menthyl lactate, *Mimosa tenuiflora, Nymphaea alba*, olaflur, *Oryza sativa*, panthenol, paraffinum liquidum, PEG-20M, PEG-26 jojoba acid, PEG-26 jojoba alcohol, PEG-35 castor oil, PEG-40 hydrogenated castor oil, PEG-60 hydrogenated castor oil, PEG-8 caprylic/capric acid, *Persea gratissima*, petrolatum, potassium aspartate, potassium sorbate, propylene glycol, *Prunus amygdalus dulcis, Prunus armeniaca, Prunus persica*, retinyl palmitate, *Ricinus communis, Rosa canina, Rosmarinus officinalis, Rubus idaeus*, salicylic acid, *Sambucus nigra*, sarcosine, *Serenoa serrulata, Simmondsia chinensis*, sodium carboxymethyl betaglucan, sodium cocoyl amino acids, sodium hyaluronate, sodium palmitoyl praline, stearoxytrimethylsilane, stearyl alcohol, sulfurized TEA-ricinoleate, talc, *Thymus vulgaris, Tilia cordata*, tocopherol, tocopheryl acetate, trideceth-9, *triticum vulgare*, tyrosine, undecylenoyl glycine, urea, *Vaccinium myrtillus*, valine, zinc oxide, zinc sulfate.

The preservative blends of the invention can be used in emulsions (both oil-in-water and water-in-oil), in aqueous solutions, in PIT (phase inversion temperature) emulsions, in oily solutions, in foaming cosmetic formulations (foams), and in so-called multiple emulsions, e.g. in triple emulsions (such as water/oil/water emulsions).

The preservative blends of the invention can also be formulated as creams, gels, liquids or lotions. They can be used in shampoos, hair conditioners, hair dyes, hair preparations, aftershave lotions, bath soaps and detergents, fragrance preparations, sun care products, indoor tanning products, body and hand preparations, personal cleansers, shaving preparations, tonics, dressings and other hair grooming aids, moisturizing preparations, skin care preparations, wipes and the like. These compositions can be also used in a variety of non-personal care products.

The topical formulations of the invention are prepared by adding other ingredients to a composition as defined herein, or addition to a mixture of ingredients a composition as defined herein. Alternatively, said formulations may also be made by mixing the ingredients individually or by group-wise mixing. Subsequently other specific ingredients, such as perfumes, may be added.

The present invention is further described in detail by means of the following Examples. All parts and percentages are by weight and all temperatures are degrees Celsius unless explicitly stated otherwise.

EXAMPLES

Example 1

Stability of Preservative Concentrates

Procedure: Preservative blends ETC 1-6 and comparative blends A-G as shown in Table 1 and Table 2, were prepared by mixing the components together with gentle heating. The blends were stored either in a refrigerator (2-4° C.) or a freezer (−17° C.), and then were allowed to warm up to room temperature. The characteristics of the blends at 2° C. and after freezing at −17° C. were summarized in Table 1 and Table 2.

Results: As shown in Table 1, when the total amount of salicylic acid, sorbic acid and dehydroacetic acid is less than 15 wt %, the use of co-solvent, 1,3-propanediol and glycerin helps with stabilizing these acids in benzyl alcohol at low temperatures. Although the co-solvent does not prevent freezing of the blends at −17° C., it does enable the blends to readily thaw and redissolve without or with limited mixing.

As shown in Table 2, when the total amount of salicylic acid and sorbic acid was greater than 15%, although co-solvent 1,3-propanediol was present, the blends froze after storage at 2-4° C. After the blends were stored at −17° C., crystals were settled out and mixing was needed to redissolve the precipitates.

TABLE 1

Effect of co-solvents (1,3-propanediol and glycerin) on blend characteristics upon refrigeration and freezing

| Blend # | Benzyl alcohol | Salicylic acid | Sorbic acid | Dehydroacetic acid | 1,3-propanediol | Glycerin | Characteristics at 2° C. and after freezing at −17° C. |
|---|---|---|---|---|---|---|---|
| ECT 1 | 83% | 11% | 3% | — | 3% | — | Clear sol at 2° C., crystals settled out after freeze/thaw cycle |
| ECT 2 | 83% | 4% | 3% | 7% | 3% | — | Clear sol at 2° C., crystals settled out after freeze/thaw cycle |
| ECT 3 | 83% | 8% | 3% | 3% | 3% | — | Clear sol at 2° C., crystals formed by freeze/thaw cycle re-dissolve without mixing |
| ECT 4 | 83% | 11% | 3% | — | — | 3% | Clear sol at 2° C., very few crystals formed by freeze/thaw cycle all re-dissolve without mixing |
| ECT 5 | 83% | 4% | 3% | 7% | — | 3% | Clear sol at 2° C., crystals formed by freeze/thaw cycle re-dissolve without mixing |
| ECT 6 | 83% | 8% | 3% | 3% | — | 3% | Clear sol at 2° C., least amount of crystals formed by freeze/thaw cycle all re-dissolve without mixing |

TABLE 2

Effect of co-solvent (1,3-propanediol) on blend characteristics upon refrigerated storage

| Blend (Comparative) | Benzyl alcohol | Salicylic acid | Sorbic acid | 1,3-propanediol | Characteristics after storage in refrigerator (2-4° C.) | Characteristics after freeze/thaw cycle |
|---|---|---|---|---|---|---|
| A | 81.0% | 13.0% | 6.0% | — | Froze in the cold, went back into solution with mixing | Very thick layer of crystals settled out, went back into solution after about 1 hour of mixing |
| B | 80.0% | 13.0% | 6.0% | 1.0% | Froze in the cold, went back into solution with mixing | Thick layer of crystals settled out, went back into solution after about 40 minutes of mixing |
| C | 81.0% | 12.5% | 5.5% | 1.0% | Froze in the cold, went back into solution with mixing | A layer of crystals settled out, went back into solution after about 10 minutes of mixing |
| D | 79.0% | 13.0% | 6.0% | 2.0% | Did not completely freeze (slushy), went back into solution with mixing | Very thick layer of crystals settled out, went back into solution after about 10 minutes of mixing |
| E | 80.0% | 12.5% | 5.5% | 2.0% | Did not completely freeze (slushy), went back into solution with mixing | Thick layer of crystals settled out, went back into solution after about 10 minutes of mixing |
| F | 80.0% | 12.0% | 5.0% | 3.0% | Did not freeze, a few crystals ppt, went back into solution with mixing | A thin layer of crystals settled out, went back into solution after about 5 minutes of mixing |
| G | 79.0% | 12.5% | 5.5% | 3.0% | Froze, but very rapidly melted to give a solution with | A thin layer of crystals settled out, went back into |

TABLE 2-continued

Effect of co-solvent (1,3-propanediol) on blend characteristics upon refrigerated storage

| Blend (Comparative) | Benzyl alcohol | Salicylic acid | Sorbic acid | 1,3-propanediol | Characteristics after storage in refrigerator (2-4° C.) | Characteristics after freeze/thaw cycle |
|---|---|---|---|---|---|---|
| | | | | | a few crystals ppt, went back into solution with mixing | solution after about 10 minutes of mixing |

Example 2

Microbiological Efficacy—1% Preservation Blends

CTFA Challenge Test Procedure: A challenge protocol similar to the CTFA method was followed to assess efficacy against a broad spectrum of microorganisms. The five separate inocula were: *Staphylococcus aureus* (ATCC 6538), mixed *Pseudomonas aeruginosa* (ATCC 9027) and *Burkholderia cepacia* (ATCC 25416), mixed *Klebsiella pneumoniae* (ATCC 4352) and *Enterobacter gergoviae* (ATCC 33028), *Candida albicans* (ATCC 10231), and a mixture of molds: *Aspergillus niger* (ATCC 16404) and 2 *Penicillium* sp. isolated from cosmetic products. Samples (35 grams each) were inoculated with approximately 2,000,000 bacteria per gram or 100,000 yeast cells or mold spores per gram. Individual challenges were prepared from overnight slants of bacteria and yeast cultures and from heavily sporulating mold cultures, 7 to 10 days old. All samples were plated quantitatively for viable organisms after 24 hours and weekly for up to 4 weeks. Samples inoculated with mold spores were also plated after 48 hours. Samples were re-challenged after four weeks (or sooner where appropriate) and the same sampling regime followed.

Recommended "Pass" Criteria: CTFA recommends at least a 99.9% reduction of vegetative bacteria and at least a 90% reduction of yeasts and molds within 7 days following each challenge with no increase in count thereafter.

Test Formulations:

The formulations used to demonstrate the efficacy of our blends were as follows.
  i. Oil in water lotion, pH 6.5, AR12-034
  ii. Hair Conditioner, pH 3.99, AR13-069 (same as AR5-024)
  iii. Make-up Remover, pH 5.15, AR12-067 (Ref # KKL9-181)
  iv. Lotion, pH 7.85, KKL 14-46
  v. Water in Oil Emulsion, pH N/A, AR12-068
  vi. Make-up Remover, pH 8.1, KKL 14-45

The preservative concentrates were added to these formulations to give a final concentration of 1%.

Summary of Test Results:

(i) Oil in Water Lotion, pH 6.5, AR12-034 (Data Shown in Tables 3 Through 5d)

Initial screen with ECT1, ECT2 and ECT 3 blends showed excellent reduction of all challenge organisms occurred within 24 hours in the preserved samples and all were reduced to <10 cfu/g within one week, whereas the unpreserved controls had high counts during the test period.

TABLE 3

Inoculum-Colony Forming Units Added per Gram (CFU/g) of Oil in water lotion pH 6.5

| Organism | Challenge #1 CFU/g | Challenge #2 CFU/g |
|---|---|---|
| S. aureus | $2.9 \times 10^6$ | $1.6 \times 10^6$ |
| K. pneumoniae + E. gergoviae | $4.0 \times 10^6$ | $2.9 \times 10^6$ |
| P. aeruginosa + B. cepacia | $2.0 \times 10^6$ | $1.2 \times 10^6$ |
| C. albicans | $8.5 \times 10^4$ | $1.6 \times 10^5$ |
| Mixed Mold | $9.0 \times 10^4$ | $9.0 \times 10^4$ |

TABLE 4

Inoculum Recovered from Unpreserved Oil in water lotion pH 6.5 at '0' Hour-Colony Forming Units per Gram (CFU/g)

| Organism | Challenge #1 CFU/g | Challenge #2 CFU/g |
|---|---|---|
| S. aureus | $1.3 \times 10^6$ | $1.9 \times 10^6$ |
| K. pneumoniae + E. gergoviae | $3.1 \times 10^6$ | $7.0 \times 10^6$ |
| P. aeruginosa + B. cepacia | $7.9 \times 10^4$ | $4.2 \times 10^6$ |
| C. albicans | $6.8 \times 10^4$ | $1.3 \times 10^5$ |
| Mixed Mold | $8.0 \times 10^4$ | $7.0 \times 10^4$ |

TABLE 5a

Unpreserved Oil in water lotion pH 6.5- Colony Forming Units per Gram (CFU/g)

| | Challenge #1 | | | | Challenge #2 | | | |
|---|---|---|---|---|---|---|---|---|
| Organism | 24 Hours | 48 Hours | 1 Week | 2 Weeks | 24 Hours | 48 Hours | 1 Week | 2 Weeks |
| S. aureus | $1.4 \times 10^6$ | — | $4.8 \times 10^5$ | $3.3 \times 10^4$ | $2.1 \times 10^6$ | — | $1.1 \times 10^6$ | $6.0 \times 10^3$ |
| K. pneumoniae + E. gergoviae | $9.4 \times 10^5$ | — | $3.0 \times 10^6$ | $1.4 \times 10^6$ | $5.9 \times 10^6$ | — | $4.5 \times 10^6$ | $9.9 \times 10^5$ |
| P. aeruginosa + B. cepacia | $<10^2$ | — | $1.6 \times 10^2$ | $<10$ | $2.4 \times 10^6$ | — | $2.8 \times 10^6$ | $1.8 \times 10^6$ |

TABLE 5a-continued

Unpreserved Oil in water lotion pH 6.5-
Colony Forming Units per Gram (CFU/g)

| Organism | Challenge #1 | | | | Challenge #2 | | | |
| --- | --- | --- | --- | --- | --- | --- | --- | --- |
| | 24 Hours | 48 Hours | 1 Week | 2 Weeks | 24 Hours | 48 Hours | 1 Week | 2 Weeks |
| C. albicans | $3.6 \times 10^4$ | — | $2.0 \times 10^4$ | $2.6 \times 10^4$ | $8.0 \times 10^4$ | — | $8.9 \times 10^4$ | $8.0 \times 10^4$ |
| Mixed Mold | $1.8 \times 10^4$ | $1.1 \times 10^4$ | $1.7 \times 10^4$ | $3.0 \times 10^4$ | $2.8 \times 10^4$ | $2.0 \times 10^4$ | $2.0 \times 10^4$ | $2.8 \times 10^4$ |

TABLE 5b

Oil in water lotion pH 6.5 with 1% ECT-1-
Colony Forming Units per Gram (CFU/g)

| Organism | Challenge #1 | | | | Challenge #2 | | | |
| --- | --- | --- | --- | --- | --- | --- | --- | --- |
| | 24 Hours | 48 Hours | 1 Week | 2 Weeks | 24 Hours | 48 Hours | 1 Week | 2 Weeks |
| S. aureus | <10 | — | <10 | <10 | <10 | — | <10 | <10 |
| K. pneumoniae + E. gergoviae | <10 | — | <10 | <10 | <10* | — | <10 | <10 |
| P. aeruginosa + B. cepacia | <10 | — | <10 | <10 | <10 | — | <10 | <10 |
| C. albicans | $3.0 \times 10^1$ | — | <10 | <10 | <10 | — | <10 | <10 |
| Mixed Mold | $1.0 \times 10^3$ | $2.0 \times 10^1$ | <10 | <10 | $2.0 \times 10^2$ | $6.0 \times 10^1$ | <10 | <10 |

*Bacillus contamination

TABLE 5c

Oil in water lotion pH 6.5 with 1% ECT-2 - Colony Forming Units per Gram (CFU/g)

| Organism | Challenge #1 | | | | Challenge #2 | | | |
| --- | --- | --- | --- | --- | --- | --- | --- | --- |
| | 24 Hours | 48 Hours | 1 Week | 2 Weeks | 24 Hours | 48 Hours | 1 Week | 2 Weeks |
| S. aureus | $7.9 \times 10^4$ | — | <10 | <10 | $4.9 \times 10^4$ | — | <10 | <10 |
| K. pneumoniae + E. gergoviae | <10 | — | <10 | <10 | <10 | — | <10 | <10 |
| P. aeruginosa + B. cepacia | <10 | — | <10 | <10 | <10 | — | <10 | <10 |
| C. albicans | $2.9 \times 10^3$ | — | <10 | <10 | $1.8 \times 10^4$ | — | <10 | <10 |
| Mixed Mold | $1.2 \times 10^4$ | $1.0 \times 10^2$ | <10 | <10* | $5.0 \times 10^3$ | $8.0 \times 10^1$ | <10 | <10 |

*Bacillus contamination

TABLE 5d

Oil in water lotion pH 6.5 with 1% ECT3- Colony Forming Units per Gram (CFU/g)

| Organism | Challenge #1 | | | | Challenge #2 | | | |
| --- | --- | --- | --- | --- | --- | --- | --- | --- |
| | 24 Hours | 48 Hours | 1 Week | 2 Weeks | 24 Hours | 48 Hours | 1 Week | 2 Weeks |
| S. aureus | $1.1 \times 10^2$ | — | <10 | <10 | $9.0 \times 10^1$ | — | <10 | <10 |
| K. pneumoniae + E. gergoviae | <10 | — | <10 | <10 | <10 | — | <10 | <10 |
| P. aeruginosa + B. cepacia | <10 | — | <10 | <10 | <10 | — | <10 | <10 |
| C. albicans | $1.8 \times 10^3$ | — | <10 | <10 | $1.4 \times 10^4$ | — | <10 | <10 |
| Mixed Mold | $6.0 \times 10^3$ | $4.0 \times 10^1$ | <10 | <10 | $1.7 \times 10^3$ | <10 | <10 | <10 |

(ii) Hair Conditioner, pH 3.99, AR 13-069 (Same as AR5-024) (Data Shown in Tables 6 Through 8c)

Excellent reduction of all challenge organisms occurred within 24 hours in the preserved samples and all were reduced to <10 cfu/g within one week. Although *S. aureus* died off within one week in the unpreserved samples, efficacy of the preservatives against this organism was obvious at the 24 hour sampling time.

TABLE 6

Inoculum-Colony Forming Units Added per Gram (CFU/g) of Hair Conditioner

| Organism | Challenge #1 CFU/g | Challenge #2 CFU/g |
|---|---|---|
| S. aureus | $2.1 \times 10^6$ | $2.6 \times 10^6$ |
| K. pneumoniae + E. gergoviae | $4.0 \times 10^6$ | $3.5 \times 10^6$ |
| P. aeruginosa + B. cepacia | $3.8 \times 10^6$ | $4.4 \times 10^6$ |

TABLE 6-continued

Inoculum-Colony Forming Units Added per Gram (CFU/g) of Hair Conditioner

| Organism | Challenge #1 CFU/g | Challenge #2 CFU/g |
|---|---|---|
| C. albicans | $4.8 \times 10^4$ | $1.7 \times 10^4$ |
| Mixed Mold | $1.4 \times 10^5$ | $1.0 \times 10^5$ |

TABLE 7

Inoculum Recovered from Unpreserved Hair Conditioner at '0' Hour-Colony Forming Units per Gram (CFU/g)

| Organism | Challenge #1 CFU/g | Challenge #2 CFU/g |
|---|---|---|
| S. aureus | $9.2 \times 10^5$ | $1.0 \times 10^5$ |
| K. pneumoniae + E. gergoviae | $1.4 \times 10^6$ | $2.7 \times 10^8$ |
| P. aeruginosa + B. cepacia | $1.4 \times 10^6$ | $1.0 \times 10^8$ |
| C. albicans | $3.1 \times 10^4$ | $1.9 \times 10^7$ |
| Mixed Mold | $4.8 \times 10^4$ | $2.9 \times 10^4$ |

TABLE 8a

Unpreserved Hair Conditioner- Colony Forming Units per Gram (CFU/g)

| | Challenge #1 | | | | | |
|---|---|---|---|---|---|---|
| Organism | 24 Hours | 48 Hours | 1 Week | 2 Weeks | 3 Weeks | 4 Weeks |
| S. aureus | $3.5 \times 10^5$ | — | <10 | <10 | <10 | <10 |
| K. pneumoniae + E. gergoviae | $9.4 \times 10^5$ | — | $3.4 \times 10^5$ | $9.0 \times 10^7$ | $2.2 \times 10^8$ | $2.6 \times 10^8$ |
| P. aeruginosa + B. cepacia | $4.9 \times 10^5$ | — | $>10^6$ | $2.1 \times 10^8$ | $6.0 \times 10^8$ | $3.0 \times 10^8$ |
| C. albicans | $3.3 \times 10^5$ | — | $3.3 \times 10^6$ | $2.7 \times 10^6$ | $1.9 \times 10^6$ | $2.7 \times 10^6$ |
| Mixed Mold | $2.1 \times 10^4$ | $1.7 \times 10^4$ | $3.5 \times 10^3$ | $2.3 \times 10^3$ | $1.1 \times 10^3$ | $1.2 \times 10^3$ |

| | Challenge #2 | | | | | |
|---|---|---|---|---|---|---|
| Organism | 24 Hours | 48 Hours | 1 Week | 2 Weeks | 3 Weeks | 4 Weeks |
| S. aureus | $3.5 \times 10^5$ | — | <10 | <10 | <10 | <10 |
| K. pneumoniae + E. gergoviae | $9.4 \times 10^5$ | — | $1.2 \times 10^8$ | $5.5 \times 10^7$ | $1.4 \times 10^7$ | $3.5 \times 10^6$ |
| P. aeruginosa + B. cepacia | $4.9 \times 10^5$ | — | $5.6 \times 10^8$ | $>10^8$ | $>10^8$ | $>10^8$ |
| C. albicans | $3.3 \times 10^5$ | — | $2.0 \times 10^7$ | $2.0 \times 10^7$ | $6.2 \times 10^6$ | $2.8 \times 10^7$ |
| Mixed Mold | $2.1 \times 10^4$ | $2.0 \times 10^4$ | $6.0 \times 10^3$ | $2.6 \times 10^4$ | $3.6 \times 10^4$ | $1.4 \times 10^4$ |

TABLE 8b

Hair Conditioner with 1% ECT-4 - Colony Forming Units per Gram (CFU/g)

| | Challenge #1 | | | | | | Challenge #2 | | | | | |
|---|---|---|---|---|---|---|---|---|---|---|---|---|
| Organism | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | <10 | — | <10 | <10 | <10 | <10 | <10 | — | <10 | <10 | <10 | <10 |
| K. pneumoniae + E. gergoviae | <10 | — | <10 | <10 | <10 | <10 | <10 | — | <10 | <10 | <10 | <10 |
| P. aeruginosa + B. cepacia | $2.0 \times 10^2$ | — | <10 | <10 | <10 | <10 | <10 | — | <10 | <10 | <10 | <10 |
| C. albicans | $6.0 \times 10^1$ | — | <10 | <10 | <10 | <10 | <10 | — | <10 | <10 | <10 | <10 |
| Mixed Mold | <10 | <10 | <10 | <10 | <10 | <10 | <10 | <10 | <10 | <10 | <10 | <10 |

TABLE 8c

Hair Conditioner with 1% ECT-6 - Colony Forming Units per Gram (CFU/g)

| | Challenge #1 | | | | | | Challenge #2 | | | | | |
|---|---|---|---|---|---|---|---|---|---|---|---|---|
| Organism | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | <10 | — | <10 | <10 | <10 | <10 | <10 | — | <10 | <10 | <10 | <10 |
| K. pneumoniae + E. gergoviae | <10 | — | <10 | <10 | <10 | <10 | <10 | — | <10 | <10 | <10 | <10 |
| P. aeruginosa + B. cepacia | $1.2 \times 10^2$ | — | <10 | <10 | <10 | <10 | <10 | — | <10 | <10 | <10 | <10 |
| C. albicans | <10 | — | <10 | <10 | <10 | <10 | <10 | — | <10 | <10 | <10 | <10 |
| Mixed Mold | <10 | <10 | <10 | <10 | <10 | <10 | <10 | <10 | <10 | <10 | <10 | <10 |

(iii) Make-Up Remover, pH 5.15, AR12-067 (Data Shown in Tables 9 Through 11c)

Excellent reduction of all challenge organisms occurred within 24 hours in the preserved samples and all were reduced to <10 cfu/g within one week. *S. aureus* and the *K. pneumoniae/E. gergoviae* inocula died off within one week in the unpreserved sample. The short survival time of these organisms makes the results somewhat inconclusive but there is some evidence for efficacy at the 24 hour sampling time.

TABLE 9

Inoculum-Colony Forming Units Added per Gram (CFU/g) of Make-up Remover

| Organism | Challenge #1 CFU/g | Challenge #2 CFU/g |
|---|---|---|
| S. aureus | $2.1 \times 10^6$ | $2.6 \times 10^6$ |
| K. pneumoniae + E. gergoviae | $4.0 \times 10^6$ | $3.5 \times 10^6$ |
| P. aeruginosa + B. cepacia | $3.8 \times 10^6$ | $4.4 \times 10^6$ |
| C. albicans | $4.8 \times 10^4$ | $1.7 \times 10^4$ |
| Mixed Mold | $1.4 \times 10^5$ | $1.0 \times 10^5$ |

TABLE 10

Inoculum Recovered from Unpreserved Make-up Remover, pH 5.15 at '0' Hour Colony Forming Units per Gram (CFU/g)

| Organism | Challenge #1 CFU/g | Challenge #2 CFU/g |
|---|---|---|
| S. aureus | $3.4 \times 10^4$ | $5.4 \times 10^5$ |
| K. pneumoniae + E. gergoviae | $6.0 \times 10^5$ | $3.7 \times 10^5$ |
| P. aeruginosa + B. cepacia | $9.4 \times 10^5$ | $1.8 \times 10^5$ |
| C. albicans | $2.9 \times 10^5$ | $9.1 \times 10^5$ |
| Mixed Mold | $7.0 \times 10^4$ | $7.3 \times 10^4$ |

TABLE 11a

Unpreserved Make-up Remover, pH 5.15 - Colony Forming Units per Gram (CFU/g)

| | Challenge #1 | | | | | |
|---|---|---|---|---|---|---|
| Organism | 24 Hours | 48 Hours | 1 Week | 2 Weeks | 3 Weeks | 4 Weeks |
| S. aureus | $9.0 \times 10^1$ | — | <10 | <10 | <10 | <10 |
| K. pneumoniae + E. gergoviae | $5.3 \times 10^3$ | — | <10 | <10 | <10 | <10 |
| P. aeruginosa + B. cepacia | $3.3 \times 10^5$ | — | $1.8 \times 10^6$ | $3.5 \times 10^6$ | $1.6 \times 10^6$ | $1.4 \times 10^6$ |
| C. albicans | $1.8 \times 10^4$ | — | $1.9 \times 10^4$ | $8.0 \times 10^3$ | $1.7 \times 10^4$ | $1.2 \times 10^4$ |
| Mixed Mold | $1.5 \times 10^4$ | $5.0 \times 10^4$ | $2.4 \times 10^4$ | $1.1 \times 10^4$ | $7.0 \times 10^3$ | $1.1 \times 10^4$ |

| | Challenge #2 | | | | | |
|---|---|---|---|---|---|---|
| Organism | 24 Hours | 48 Hours | 1 Week | 2 Weeks | 3 Weeks | 4 Weeks |
| S. aureus | $7.9 \times 10^3$ | — | <10 | <10 | <10 | <10 |
| K. pneumoniae + E. gergoviae | $9.0 \times 10^1$ | — | <10 | <10 | <10 | <10 |
| P. aeruginosa + B. cepacia | $7.8 \times 10^6$ | — | $2.8 \times 10^6$ | $6.1 \times 10^6$ | $5.3 \times 10^6$ | $7.7 \times 10^6$ |
| C. albicans | $5.6 \times 10^4$ | — | $6.6 \times 10^4$ | $3.2 \times 10^4$ | $2.0 \times 10^4$ | $1.5 \times 10^4$ |
| Mixed Mold | $1.0 \times 10^5$ | $5.0 \times 10^4$ | $7.7 \times 10^4$ | $4.2 \times 10^4$ | $3.3 \times 10^4$ | $7.0 \times 10^4$ |

TABLE 11b

Make-up Remover with 1% ECT-4, pH 5.15 - Colony Forming Units per Gram (CFU/g)

| | Challenge #1 | | | | | | Challenge #2 | | | | | |
|---|---|---|---|---|---|---|---|---|---|---|---|---|
| Organism | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | $2.0 \times 10^1$ | — | <10 | <10 | <10 | <10 | <10 | — | <10 | <10 | <10 | <10 |
| K. pneumoniae + E. gergoviae | $4.0 \times 10^1$ | — | <10 | <10 | <10 | <10 | <10 | — | <10 | <10 | <10 | <10 |
| P. aeruginosa + B. cepacia | $1.0 \times 10^1$ | — | <10 | <10 | <10 | <10 | <10 | — | <10 | <10 | <10 | <10 |
| C. albicans | <10 | — | <10 | <10 | <10 | <10 | <10 | — | <10 | <10 | <10 | <10 |
| Mixed Mold | <10 | <10 | <10 | <10 | <10 | <10 | <10 | <10 | <10 | <10 | <10 | <10 |

TABLE 11c

Make-up Remover with 1% ECT-6, pH 5.15 - Colony Forming Units per Gram (CFU/g)

| | Challenge #1 | | | | | | Challenge #2 | | | | | |
|---|---|---|---|---|---|---|---|---|---|---|---|---|
| Organism | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | $9.0 \times 10^1$ | — | <10 | <10 | <10 | <10 | <10 | — | <10 | <10 | <10 | <10 |
| K. pneumoniae + E. gergoviae | <10 | — | <10 | <10 | <10 | <10 | <10 | — | <10 | <10 | <10 | <10 |
| P. aeruginosa + B. cepacia | <10 | — | <10 | <10 | <10 | <10 | <10 | — | <10 | <10 | <10 | <10 |
| C. albicans | <10 | — | <10 | <10 | <10 | <10 | <10 | — | <10 | <10 | <10 | <10 |
| Mixed Mold | <10 | <10 | <10 | <10 | <10 | <10 | <10 | <10 | <10 | <10 | <10 | <10 |

(iv) Lotion, pH 7.85, KKL 14-46 (Data Shown in Tables 12 Through 14c)

Excellent reduction of all challenge organisms occurred within 24 hours in the preserved samples and all were reduced to <10 cfu/g within one week. This formula is more difficult to preserve than the other four products being tested. All the challenge organisms are surviving in the unpreserved control and the P. aeruginosa/B. cepacia increased by >90% between weeks one and two.

TABLE 12

Inoculum-Colony Forming Units Added per Gram (CFU/g) of Product

| Organism | Challenge #1 CFU/g | Challenge #2 CFU/g |
|---|---|---|
| S. aureus | $1.8 \times 10^6$ | $1.4 \times 10^6$ |
| K. pneumoniae + E. gergoviae | $3.3 \times 10^6$ | $2.7 \times 10^6$ |
| P. aeruginosa + B. cepacia | $4.0 \times 10^6$ | $2.1 \times 10^6$ |
| C. albicans | $1.7 \times 10^5$ | $1.2 \times 10^5$ |
| Mixed Mold | $2.3 \times 10^5$ | $1.9 \times 10^5$ |

TABLE 13

Inoculum Recovered from Unpreserved pH 7.85 Lotion at '0' Hour- Colony Forming Units per Gram (CFU/g)

| Organism | Challenge #1 CFU/g | Challenge #2 CFU/g |
|---|---|---|
| S. aureus | $2.3 \times 10^6$ | $1.7 \times 10^6$ |
| K. pneumoniae + E. gergoviae | $2.9 \times 10^6$ | $3.1 \times 10^6$ |
| P. aeruginosa + B. cepacia | $2.3 \times 10^6$ | $7.6 \times 10^7$ |
| C. albicans | $1.3 \times 10^5$ | $1.8 \times 10^5$ |
| Mixed Mold | $3.5 \times 10^5$ | $2.8 \times 10^5$ |

TABLE 14a

Unpreserved pH 7.85 Lotion - Colony Forming Units per Gram (CFU/g)

| | Challenge #1 | | | | | |
|---|---|---|---|---|---|---|
| Organism | 24 Hours | 48 Hours | 1 Week | 2 Weeks | 3 Weeks | 4 Weeks |
| S. aureus | $1.3 \times 10^6$ | — | $1.6 \times 10^4$ | $1.1 \times 10^4$ | $2.0 \times 10^4$ | $3.0 \times 10^4$ |
| K. pneumoniae + E. gergoviae | $1.3 \times 10^6$ | — | $9.5 \times 10^5$ | $1.8 \times 10^6$ | $5.4 \times 10^5$ | $7.0 \times 10^5$ |

TABLE 14a-continued

Unpreserved pH 7.85 Lotion - Colony Forming Units per Gram (CFU/g)

| | | | | | | |
|---|---|---|---|---|---|---|
| P. aeruginosa + B. cepacia | >$10^6$ | — | $8.5 \times 10^6$ | $1.2 \times 10^8$ | >$10^8$ | $4.3 \times 10^7$ |
| C. albicans | $1.1 \times 10^5$ | — | $1.0 \times 10^5$ | $3.0 \times 10^{5*}$ | $1.9 \times 10^6$ | $9.0 \times 10^6$ |
| Mixed Mold | $2.3 \times 10^6$ | $2.6 \times 10^5$ | $9.0 \times 10^4$ | $3.6 \times 10^5$ | $5.9 \times 10^{4*}$ | $1.6 \times 10^{4*}$ |

| | Challenge #2 | | | | | |
|---|---|---|---|---|---|---|
| Organism | 24 Hours | 48 Hours | 1 Week | 2 Weeks | 3 Weeks | 4 Weeks |
| S. aureus | $1.6 \times 10^6$ | — | $1.6 \times 10^4$ | $9.5 \times 10^3$ | $6.0 \times 10^3$ | $8.0 \times 10^3$ |
| K. pneumoniae + E. gergoviae | $4.9 \times 10^6$ | — | $6.7 \times 10^5$ | $7.3 \times 10^4$ | $5.1 \times 10^3$ | $2.3 \times 10^3$ |
| P. aeruginosa + B. cepacia | $1.1 \times 10^8$ | — | $1.6 \times 10^8$ | $1.2 \times 10^8$ | $9.5 \times 10^7$ | $9.8 \times 10^7$ |
| C. albicans | $2.8 \times 10^5$ | — | $2.0 \times 10^5$ | $1.7 \times 10^5$ | $9.5 \times 10^4$ | $1.5 \times 10^5$ |
| Mixed Mold | $1.1 \times 10^6$ | $5.2 \times 10^{5*}$ | $3.7 \times 10^4$ | $2.8 \times 10^5$ | $7.0 \times 10^4$ | $7.0 \times 10^4$ |

*Bacterial Contamination

TABLE 14b pH 7.85 Lotion with 1% ECT-4 - Colony Forming Units per Gram (CFU/g)

| | Challenge #1 | | | | | | Challenge #2 | | | | | |
|---|---|---|---|---|---|---|---|---|---|---|---|---|
| Organism | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | $7.0 \times 10^1$ | — | <10 | <10 | <10 | <10 | <10 | — | <10 | <10 | <10 | <10 |
| K. pneumoniae + E. gergoviae | $2.0 \times 10^1$ | — | <10 | <10 | <10 | <10 | <10 | — | <10 | <10 | <10 | <10 |
| P. aeruginosa + B. cepacia | <10 | — | <10 | <10 | <10 | <10 | <10 | — | <10 | <10 | <10 | <10 |
| C. albicans | $8.7 \times 10^3$ | — | <10 | <10 | <10 | <10 | $1.3 \times 10^4$ | — | <10 | <10 | <10 | <10 |
| Mixed Mold | $1.8 \times 10^3$ | $1.9 \times 10^2$ | <10 | <10 | <10 | <10 | $9.0 \times 10^2$ | $2.1 \times 10^2$ | <10 | <10 | <10 | <10 |

TABLE 14c pH 7.85 Lotion with 1% ECT-6 - Colony Forming Units per Gram (CFU/g)

| | Challenge #1 | | | | | | Challenge #2 | | | | | |
|---|---|---|---|---|---|---|---|---|---|---|---|---|
| Organism | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | <10 | — | <10 | <10 | <10 | <10 | <10 | — | <10 | <10 | <10 | <10 |
| K. pneumoniae + E. gergoviae | <10 | — | <10 | <10 | <10 | <10 | <10 | — | <10 | <10 | <10 | <10 |
| P. aeruginosa + B. cepacia | <10 | — | <10 | <10 | <10 | <10 | <10 | — | <10 | <10 | <10 | <10 |
| C. albicans | $2.5 \times 10^3$ | — | <10 | <10 | <10 | <10 | $7.7 \times 10^3$ | — | <10 | <10 | <10 | <10 |
| Mixed Mold | $6.5 \times 10^2$ | $2.0 \times 10^1$ | <10 | <10 | <10 | <10 | $4.8 \times 10^2$ | $5.0 \times 10^1$ | <10 | <10 | <10 | <10 |

(v) Water in Oil Emulsion, pH N/A, AR 12-068 (Data Shown in Tables 15 Through 17c)

Although S. aureus and the K. pneumoniae/E. gergoviae inocula died off within one week in the unpreserved sample and the P. aeruginosa/B. cepacia was reduced to <10 cfu/g within two weeks, all the challenge organisms in the preserved samples were reduced to <10 cfu/g within 24 hours.

TABLE 15

Inoculum-Colony Forming Units Added per Gram (CFU/g) of Product

| Organism | Challenge #1 CFU/g | Challenge #2 CFU/g |
|---|---|---|
| S. aureus | $1.8 \times 10^6$ | $1.4 \times 10^6$ |
| K. pneumoniae + E. gergoviae | $2.7 \times 10^6$ | $2.7 \times 10^6$ |
| P. aeruginosa + B. cepacia | $1.9 \times 10^6$ | $2.1 \times 10^6$ |
| C. albicans | $1.4 \times 10^5$ | $1.2 \times 10^5$ |
| Mixed Mold | $1.5 \times 10^5$ | $1.9 \times 10^5$ |

TABLE 16

Inoculum Recovered from Unpreserved Water in Oil Emulsion at '0' Hour - Colony Forming Units per Gram (CFU/g)

| Organism | Challenge #1 CFU/g | Challenge #2 CFU/g |
|---|---|---|
| S. aureus | $1.8 \times 10^5$ | $6.6 \times 10^5$ |
| K. pneumoniae + E. gergoviae | $2.5 \times 10^5$ | $1.2 \times 10^6$ |
| P. aeruginosa + B. cepacia | $2.9 \times 10^5$ | $1.8 \times 10^5$ |
| C. albicans | $2.5 \times 10^5$ | $3.2 \times 10^4$ |
| Mixed Mold | $2.7 \times 10^4$ | $9.0 \times 10^3$ |

TABLE 17a

Unpreserved Water in Oil Emulsion - Colony Forming Units per Gram (CFU/g)

| Organism | 24 Hours | 48 Hours | 1 Week | 2 Weeks | 3 Weeks | 4 Weeks |
|---|---|---|---|---|---|---|
| Challenge #1 | | | | | | |
| S. aureus | $8.6 \times 10^4$ | — | <10 | <10 | <10 | <10 |
| K. pneumoniae + E. gergoviae | $5.6 \times 10^4$ | — | <10 | <10 | <10 | <10 |
| P. aeruginosa + B. cepacia | $3.1 \times 10^4$ | — | $2.9 \times 10^3$ | <10 | <10 | <10 |
| C. albicans | $4.6 \times 10^4$ | — | $1.3 \times 10^4$ | $1.6 \times 10^4$ | $1.1 \times 10^4$ | $2.9 \times 10^3$ |
| Mixed Mold | $1.2 \times 10^4$ | $2.5 \times 10^4$ | $9.7 \times 10^3$ | $3.3 \times 10^3$ | $4.0 \times 10^3$ | $7.0 \times 10^3$ |
| Challenge #2 | | | | | | |
| S. aureus | $9.9 \times 10^4$ | — | <10 | <10 | <10 | <10 |
| K. pneumoniae + E. gergoviae | $9.7 \times 10^4$ | — | <10 | <10 | <10 | <10 |
| P. aeruginosa + B. cepacia | $5.6 \times 10^5$ | — | $2.0 \times 10^4$ | $>10^4$ | $6.8 \times 10^5$ | $3.4 \times 10^5$ |
| C. albicans | $1.0 \times 10^5$ | — | $5.0 \times 10^4$ | $7.2 \times 10^4$ | $1.4 \times 10^5$ | $5.3 \times 10^4$ |
| Mixed Mold | $1.0 \times 10^5$ | $2.6 \times 10^4$ | $6.6 \times 10^4$ | $2.1 \times 10^4$ | $4.1 \times 10^4$ | $3.4 \times 10^5$ |

TABLE 17b

Water in Oil Emulsion with 1% ECT-4 - Colony Forming Units per Gram (CFU/g)

| Organism | Challenge #1 | | | | | | Challenge #2 | | | | | |
|---|---|---|---|---|---|---|---|---|---|---|---|---|
| | 24 Hours | 48 Hours | 1 Week | 2 Weeks | 3 Weeks | 4 Weeks | 24 Hours | 48 Hours | 1 Week | 2 Week | 3 Weeks | 4 Weeks |
| S. aureus | <10 | — | <10 | <10 | <10 | <10 | <10 | — | <10 | <10 | <10 | <10 |
| K. pneumoniae + E. gergoviae | <10 | — | <10 | <10 | <10 | <10 | <10 | — | <10 | <10 | <10 | <10 |
| P. aeruginosa + B. cepacia | <10 | — | <10 | <10 | <10 | <10 | <10 | — | <10 | <10 | <10 | <10 |
| C. albicans | <10 | — | <10 | <10 | <10 | <10 | <10 | — | <10 | <10 | <10 | <10 |
| Mixed Mold | <10 | <10 | <10 | <10 | <10 | <10 | <10 | <10 | <10 | <10 | <10 | <10 |

TABLE 17c

Water in Oil Emulsion with 1% ECT-6 - Colony Forming Units per Gram (CFU/g)

| Organism | Challenge #1 | | | | | | Challenge #2 | | | | | |
|---|---|---|---|---|---|---|---|---|---|---|---|---|
| | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | <10 | — | <10 | <10 | <10 | <10 | <10 | — | <10 | <10 | <10 | <10 |
| K. pneumoniae + E. gergoviae | <10 | — | <10 | <10 | <10 | <10 | <10 | — | <10 | <10 | <10 | <10 |

TABLE 17c-continued

Water in Oil Emulsion with 1% ECT-6 - Colony Forming Units per Gram (CFU/g)

| | Challenge #1 | | | | | | Challenge #2 | | | | |
|---|---|---|---|---|---|---|---|---|---|---|---|
| Organism | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| P. aeruginosa + B. cepacia | <10 | — | <10 | <10 | <10 | <10 | <10 | — | <10 | <10 | <10 | <10 |
| C. albicans | <10 | — | <10 | <10 | <10 | <10 | <10 | — | <10 | <10 | <10 | <10 |
| Mixed Mold | <10 | <10 | <10 | <10 | <10 | <10 | <10 | <10 | <10 | <10 | <10 | <10 |

(vi) Make-Up Remover, pH 8.1, KKL 14-45 (Data Shown in Tables 18 Through 20c)

Excellent reduction of all challenge organisms occurred within 24 hours in the preserved samples and all were reduced to 10 cfu/g within one week. Although S. aureus and C. albicans died off within one week in the unpreserved sample, there was some differentiation between preserved and unpreserved samples at 24 hours.

TABLE 18

Inoculum - Colony Forming Units Added per Gram (CFU/g) of Make-up Remover, pH 8.1

| Organism | Challenge #1 CFU/g | Challenge #2 CFU/g |
|---|---|---|
| S. aureus | $2.4 \times 10^6$ | $4.4 \times 10^6$ |
| K. pneumoniae + E. gergoviae | $4.0 \times 10^6$ | $4.0 \times 10^6$ |
| P. aeruginosa + B. cepacia | $3.8 \times 10^6$ | $5.1 \times 10^6$ |
| C. albicans | $1.3 \times 10^5$ | $4.2 \times 10^5$ |
| Mixed Mold | $2.3 \times 10^5$ | $4.3 \times 10^5$ |

TABLE 19

Inoculum Recovered from Make-up Remover, pH 8.1 at '0' Hour - Colony Forming Units per Gram (CFU/g)

| Organism | Challenge #1 CFU/g | Challenge #2 CFU/g |
|---|---|---|
| S. aureus | $7.3 \times 10^5$ | $9.4 \times 10^5$ |
| K. pneumoniae + E. gergoviae | $9.4 \times 10^5$ | $8.8 \times 10^6$ |
| P. aeruginosa + B. cepacia | $7.0 \times 10^5$ | $6.2 \times 10^6$ |
| C. albicans | $3.4 \times 10^4$ | $2.2 \times 10^5$ |
| Mixed Mold | $6.3 \times 10^4$ | $1.3 \times 10^5$ |

TABLE 20a

Unpreserved Make-up Remover, pH 8.1 - Colony Forming Units per Gram (CFU/g)

| | Challenge #1 | | | | | |
|---|---|---|---|---|---|---|
| Organism | 24 Hours | 48 Hours | 1 Week | 2 Weeks | 3 Weeks | 4 Weeks |
| S. aureus | $1.0 \times 10^2$ | — | <10 | <10 | <10 | <10 |
| K. pneumoniae + E. gergoviae | $5.1 \times 10^6$ | — | $8.0 \times 10^6$ | $6.8 \times 10^6$ | $7.0 \times 10^6$ | $2.5 \times 10^6$ |
| P. aeruginosa + B. cepacia | $4.5 \times 10^6$ | — | $6.6 \times 10^6$ | $1.5 \times 10^6$ | $1.6 \times 10^6$ | $1.5 \times 10^6$ |
| C. albicans | $4.0 \times 10^2$ | — | <10 | <10 | <10 | <10 |
| Mixed Mold | $1.1 \times 10^4$ | $3.7 \times 10^4$ | $2.5 \times 10^4$ | $2.9 \times 10^4$ | $7.0 \times 10^4$ | $2.0 \times 10^4$ |

| | Challenge #2 | | | | | |
|---|---|---|---|---|---|---|
| Organism | 24 Hours | 48 Hours | 1 Week | 2 Weeks | 3 Weeks | 4 Weeks |
| S. aureus | <10 | — | <10 | <10 | <10 | <10 |
| K. pneumoniae + E. gergoviae | $5.5 \times 10^6$ | — | $9.2 \times 10^6$ | $1.7 \times 10^6$ | $2.2 \times 10^6$ | $8.0 \times 10^5$ |
| P. aeruginosa + B. cepacia | $9.8 \times 10^6$ | — | $8.7 \times 10^6$ | $2.0 \times 10^6$ | $6.8 \times 10^6$ | $3.2 \times 10^6$ |
| C. albicans | $9.1 \times 10^3$ | — | $1.4 \times 10^3$ | $2.5 \times 10^2$ | <10 | <10 |
| Mixed Mold | $2.7 \times 10^5$ | $1.0 \times 10^5$ | $1.5 \times 10^5$ | $1.0 \times 10^5$ | $1.0 \times 10^5$ | $1.0 \times 10^5$ |

TABLE 20b

Make-up Remover, pH 8.1 with 1% ECT-4 - Colony Forming Units per Gram (CFU/g)

| | Challenge #1 | | | | | | Challenge #2 | | | | | |
|---|---|---|---|---|---|---|---|---|---|---|---|---|
| Organism | 24 Hours | 48 Hours | 1 Week | 2 Weeks | 3 Weeks | 4 Weeks | 24 Hours | 48 Hours | 1 Weeks | 2 Weeks | 3 Weeks | 4 Weeks |
| S. aureus | <10 | — | <10 | <10 | <10 | <10 | <10 | — | <10 | <10 | <10 | <10 |
| K. pneumoniae + E. gergoviae | <10 | — | <10 | <10 | <10 | <10 | <10 | — | <10 | <10 | <10 | <10 |
| P. aeruginosa + B. cepacia | <10 | — | <10 | <10 | <10 | <10 | <10 | — | <10 | <10 | <10 | <10 |
| C. albicans | <10 | — | <10 | <10 | <10 | <10 | <10 | — | <10 | <10 | <10 | <10 |
| Mixed Mold | <10 | <10 | <10 | <10 | <10 | <10 | <10 | <10 | <10 | <10 | <10 | <10 |

TABLE 20c

Make-up Remover, pH 8.1 with 1% ECT-6 - Colony Forming Units per Gram (CFU/g)

| | Challenge #1 | | | | | | Challenge #2 | | | | | |
|---|---|---|---|---|---|---|---|---|---|---|---|---|
| Organism | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | <10 | — | <10 | <10 | <10 | <10 | <10 | — | <10 | <10 | <10 | <10 |
| P. aeruginosa + B. cepacia | <10 | — | <10 | <10 | <10 | <10 | <10 | — | <10 | <10 | <10 | <10 |
| K. pneumoniae + E. gergoviae | <10 | — | <10 | <10 | <10 | <10 | <10 | — | <10 | <10 | <10 | <10 |
| C. albicans | <10 | — | <10 | <10 | <10 | <10 | <10 | — | <10 | <10 | <10 | <10 |
| Mixed Mold | $7.0 \times 10^1$ | <10 | <10 | <10 | <10 | <10 | $2.6 \times 10^3$ | <10 | <10 | <10 | <10 | <10 |

Conclusions: The ECT preservative blends can effectively protect cosmetic formulations against bacterial and fungal growth, at moderate use levels even in alkaline pH.

Example 3

Microbiological Efficacy—0.6% Preservation Blends

To ascertain an effective use range, Example 2 was repeated with blend ECT 4 at 0.6% dose rate.

Summary of Test Results:

ECT 4 tested at 0.6%, was effective in 4 of the 5 personal care formulations meeting CTFA recommendations for at least a 99.9% reduction of vegetative bacteria and at least a 90% reduction of yeasts and molds within 7 days following each challenge with no increase in count thereafter. It was not however, effective in the high pH Make-up Remover formulation.

Hair Conditioner, pH 3.99, AR13-069 (Same as AR5-024) (Data Shown in Tables 21 Through 23b)

Excellent reduction of all challenge organisms occurred within 24 hours in the preserved samples. All challenge organisms were reduced to <10 cfu/g within one week following each challenge. Formulation met CTFA recommendations.

TABLE 21

Inoculum - Colony Forming Units Added per Gram (CFU/g) of Hair Conditioner

| Organism | Challenge #1 CFU/g | Challenge #2 CFU/g |
|---|---|---|
| S. aureus | $1.6 \times 10^6$ | $1.1 \times 10^6$ |
| K. pneumoniae + E. gergoviae | $1.6 \times 10^6$ | $1.9 \times 10^6$ |
| P. aeruginosa + B. cepacia | $3.4 \times 10^6$ | $1.8 \times 10^6$ |
| C. albicans | $1.5 \times 10^5$ | $8.2 \times 10^4$ |
| Mixed Mold | $7.2 \times 10^4$ | $5.7 \times 10^4$ |

TABLE 22

Inoculum Recovered from Unpreserved Hair Conditioner at '0' Hour - Colony Forming Units per Gram (CFU/g)

| Organism | Challenge #1 CFU/g | Challenge #2 CFU/g |
|---|---|---|
| S. aureus | $1.9 \times 10^6$ | $4.0 \times 10^7$ |
| K. pneumoniae + E. gergoviae | $1.2 \times 10^6$ | $1.0 \times 10^8$ |
| P. aeruginosa + B. cepacia | $2.2 \times 10^6$ | $1.5 \times 10^8$ |
| C. albicans | $2.4 \times 10^5$ | $1.3 \times 10^8$ |
| Mixed Mold | $1.0 \times 10^5$ | $8.1 \times 10^4$ |

TABLE 23a

Unpreserved Hair Conditioner - Colony Forming Units per Gram (CFU/g)

| | Challenge #1 | | | | | |
|---|---|---|---|---|---|---|
| Organism | 24 Hours | 48 Hours | 1 Week | 2 Weeks | 3 Weeks | 4 Weeks |
| S. aureus | $1.7 \times 10^4$ | — | $8.0 \times 10^6$ | $>10^7$ | $4.6 \times 10^7$ | $5.6 \times 10^7$ |
| K. pneumoniae + E. gergoviae | $3.7 \times 10^6$ | — | $>3.0 \times 10^7$ | $1.8 \times 10^8$ | $8.6 \times 10^7$ | $5.6 \times 10^7$ |
| P. aeruginosa + B. cepacia | $2.6 \times 10^7$ | — | $1.1 \times 10^8$ | $1.3 \times 10^8$ | $1.5 \times 10^8$ | $1.3 \times 10^8$ |
| C. albicans | $3.7 \times 10^5$ | — | $8.8 \times 10^6$ | $3.7 \times 10^{6*}$ ($3.4 \times 10^6$) | $7.2 \times 10^{6*}$ ($5.4 \times 10^7$) | $5.8 \times 10^{6*}$ ($7.6 \times 10^7$) |
| Mixed Mold | $3.4 \times 10^4$ | $2.2 \times 10^4$ | $3.1 \times 10^4$ | $1.0 \times 10^4$ | $3.0 \times 10^3$ | $3.9 \times 10^3$ |

| | Challenge #2 | | | | | |
|---|---|---|---|---|---|---|
| Organism | 24 Hours | 48 Hours | 1 Week | 2 Weeks | 3 Weeks | 4 Weeks |
| S. aureus | $3.6 \times 10^7$ | — | $7.1 \times 10^7$ | $4.9 \times 10^7$ | $4.9 \times 10^7$ | $3.5 \times 10^7$ |
| K. pneumoniae + E. gergoviae | $9.3 \times 10^7$ | — | $1.1 \times 10^8$ | $7.6 \times 10^7$ | $6.6 \times 10^7$ | $6.2 \times 10^7$ |
| P. aeruginosa + B. cepacia | $1.1 \times 10^8$ | — | $1.0 \times 10^8$ | $3.1 \times 10^8$ | $2.3 \times 10^8$ | $3.0 \times 10^8$ |
| C. albicans | $8.8 \times 10^{6*}$ ($1.2 \times 10^8$) | — | $5.3 \times 10^{6*}$ ($9.0 \times 10^7$) | $7.0 \times 10^{6*}$ ($1.2 \times 10^8$) | $1.1 \times 10^{6*}$ ($>3.0 \times 10^6$) | $3.8 \times 10^{6*}$ ($>3.0 \times 10^7$) |
| Mixed Mold | $3.7 \times 10^4$ | $2.8 \times 10^4$ | $2.5 \times 10^4$ | $1.2 \times 10^4$ | $1.4 \times 10^4$ | $1.1 \times 10^4$ |

TABLE 23b

Hair Conditioner with 0.6% ECT 4- Colony Forming Units per Gram (CFU/g)

| | Challenge #1 | | | | | | Challenge #2 | | | | | |
|---|---|---|---|---|---|---|---|---|---|---|---|---|
| Organism | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | <10 | — | <10 | — | — | <10 | <10 | — | <10 | <10 | <10 | <10 |
| K. pneumoniae + E. gergoviae | <10 | — | <10 | — | — | <10 | <10 | — | <10 | <10 | <10 | <10 |
| P. aeruginosa + B. cepacia | <10 | — | <10 | — | — | <10 | <10 | — | <10 | <10 | <10 | <10 |
| C. albicans | <10 | — | <10 | — | — | <10 | <10 | — | <10 | <10 | <10 | <10 |
| Mixed Mold | <10 | <10 | <10 | — | — | <10 | <10 | <10 | <10 | <10 | <10 | <10 |

Make-Up Remover, pH 5.15, AR12-067 (Ref # KKL9-181), (Data Shown in Tables 24 Through 26b)

Excellent reduction of all challenge organisms occurred within 24 hours with 0.6% ECT 4 blend. All challenge organisms were reduced to <10 cfu/g within one week following each challenge. Formulation met CTFA recommendations.

TABLE 24

Inoculum - Colony Forming Units Added per Gram (CFU/g) of Make-up Remover

| Organism | Challenge #1 CFU/g | Challenge #2 CFU/g |
|---|---|---|
| S. aureus | $1.6 \times 10^6$ | $1.1 \times 10^6$ |
| K. pneumoniae + E. gergoviae | $1.6 \times 10^6$ | $1.9 \times 10^6$ |
| P. aeruginosa + B. cepacia | $3.4 \times 10^6$ | $1.8 \times 10^6$ |

TABLE 24-continued

Inoculum - Colony Forming Units Added per Gram (CFU/g) of Make-up Remover

| Organism | Challenge #1 CFU/g | Challenge #2 CFU/g |
|---|---|---|
| C. albicans | $1.5 \times 10^5$ | $8.2 \times 10^4$ |
| Mixed Mold | $7.2 \times 10^4$ | $5.7 \times 10^4$ |

TABLE 25

Inoculum Recovered from Unpreserved Make-up Remover, pH 5.15 at '0' Hour Colony Forming Units per Gram (CFU/g)

| Organism | Challenge #1 CFU/g | Challenge #2 CFU/g |
|---|---|---|
| S. aureus | $3.7 \times 10^5$ | $6.9 \times 10^5$ |
| K. pneumoniae + E. gergoviae | $5.5 \times 10^5$ | $7.4 \times 10^5$ |
| P. aeruginosa + B. cepacia | $9.0 \times 10^5$ | $4.9 \times 10^6$ |
| C. albicans | $2.0 \times 10^5$ | $1.1 \times 10^5$ |
| Mixed Mold | $6.5 \times 10^4$ | $9.7 \times 10^4$ |

TABLE 26a

Unpreserved Make-up Remover at pH 5.15 - Colony Forming Units per Gram (CFU/g)

| | Challenge #1 | | | | | |
|---|---|---|---|---|---|---|
| Organism | 24 Hours | 48 Hours | 1 Week | 2 Weeks | 3 Weeks | 4 Weeks |
| S. aureus | $2.3 \times 10^2$ | — | <10 | <10 | <10 | <10 |
| K. pneumoniae + E. gergoviae | $2.6 \times 10^5$ | — | $1.5 \times 10^4$ | <10 | $1.0 \times 10^1$ | <10 |
| P. aeruginosa + B. cepacia | $2.8 \times 10^5$ | — | $4.3 \times 10^6$ | $5.8 \times 10^6$ | $4.3 \times 10^6$ | $2.8 \times 10^6$ |
| C. albicans | $1.3 \times 10^5$ | — | $4.3 \times 10^4$ | $5.5 \times 10^4$ | $3.8 \times 10^4$ | $4.2 \times 10^4$ |
| Mixed Mold | $6.5 \times 10^4$ | $4.1 \times 10^4$ | $6.5 \times 10^4$ | $3.2 \times 10^4$ | $6.5 \times 10^4$ | $5.7 \times 10^4$ |

| | Challenge #2 | | | | | |
|---|---|---|---|---|---|---|
| Organism | 24 Hours | 48 Hours | 1 Week | 2 Weeks | 3 Weeks | 4 Weeks |
| S. aureus | $1.7 \times 10^3$ | — | <10 | <10 | <10 | <10 |
| K. pneumoniae + E. gergoviae | $1.8 \times 10^5$ | — | $6.1 \times 10^3$ | $1.0 \times 10^1$ | <10 | <10 |
| P. aeruginosa + B. cepacia | $4.8 \times 10^6$ | — | $6.0 \times 10^6$ | $6.3 \times 10^6$ | $5.2 \times 10^6$ | $7.1 \times 10^6$ |
| C. albicans | $5.6 \times 10^4$ | — | $1.6 \times 10^{3*}$ ($>3.0 \times 10^5$) | $2.3 \times 10^{5*}$ ($>3.0 \times 10^5$) | $5.0 \times 10^{4*}$ ($4.6 \times 10^6$) | $5.2 \times 10^{4*}$ ($4.6 \times 10^6$) |
| Mixed Mold | $7.9 \times 10^4$ | $4.7 \times 10^4$ | $1.1 \times 10^5$ | $7.2 \times 10^4$ | $1.2 \times 10^5$ | $5.5 \times 10^4$ |

TABLE 26b

Make-up Remover with 0.6% ECT4, pH 5.15 - Colony Forming Units per Gram (CFU/g)

| | Challenge #1 | | | | | | Challenge #2 | | | | | |
|---|---|---|---|---|---|---|---|---|---|---|---|---|
| Organism | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | <10 | — | <10 | — | — | <10 | <10 | — | <10 | <10 | <10 | <10 |
| K. pneumoniae + E. gergoviae | <10 | — | <10 | — | — | <10 | <10 | — | <10 | <10 | <10 | <10 |
| P. aeruginosa + B. cepacia | <10 | — | <10 | — | — | <10 | <10 | — | <10 | <10 | <10 | <10 |
| C. albicans | <10 | — | <10 | — | — | <10 | <10 | — | <10 | <10 | <10 | <10 |
| Mixed Mold | $1.3 \times 10^2$ | $1.0 \times 10^1$ | <10 | — | — | <10 | <10 | <10 | <10 | <10 | <10 | <10 |

(i) Lotion, pH 7.85, KKL 14-46 (Data Shown in Tables 27 Through 29b)

This formulation was contaminated before the start of this testing and was previously noted as being more susceptible to contamination than the other four products tested. Excellent reduction of all challenge organisms by 0.6% ECT 4 occurred within 24 hours. All challenge organisms were reduced to <10 cfu/g within one week following each challenge. Formulation met CTFA recommendations.

TABLE 27

Inoculum - Colony Forming Units Added per Gram (CFU/g) of Product

| Organism | Challenge #1 CFU/g | Challenge #2 CFU/g |
|---|---|---|
| S. aureus | $1.5 \times 10^6$ | $1.6 \times 10^6$ |
| K. pneumoniae + E. gergoviae | $1.7 \times 10^6$ | $1.6 \times 10^6$ |
| P. aeruginosa + B. cepacia | $2.3 \times 10^6$ | $2.6 \times 10^6$ |

TABLE 27-continued

Inoculum - Colony Forming Units Added per Gram (CFU/g) of Product

| Organism | Challenge #1 CFU/g | Challenge #2 CFU/g |
|---|---|---|
| C. albicans | $5.2 \times 10^4$ | $7.1 \times 10^4$ |
| Mixed Mold | $1.9 \times 10^4$ | $3.9 \times 10^4$ |

TABLE 28

Inoculum Recovered from Unpreserved Lotion at '0' Hour - Colony Forming Units per Gram (CFU/g)

| Organism | Challenge #1 CFU/g | Challenge #2 CFU/g |
|---|---|---|
| S. aureus | $>3.0 \times 10^7$ | $1.5 \times 10^7$ |
| K. pneumoniae + E. gergoviae | $>3.0 \times 10^7$ | $2.1 \times 10^7$ |
| P. aeruginosa + B. cepacia | $2.9 \times 10^7$ | $1.5 \times 10^7$ |
| C. albicans | $1.0 \times 10^6$ ($2.5 \times 10^{7*}$) | $4.2 \times 10^5$ ($5.8 \times 10^{6*}$) |
| Mixed Mold | $2.3 \times 10^4$ ($>3.0 \times 10^{7*}$) | $3.0 \times 10^4$ ($6.3 \times 10^{6*}$) |

*bacterial contaminant

TABLE 29a

Unpreserved Lotion - Colony Forming Units per Gram (CFU/g)

| | Challenge #1 | | | | | |
|---|---|---|---|---|---|---|
| Organism | 24 Hours | 48 Hours | 1 Week | 2 Weeks | 3 Weeks | 4 Weeks |
| S. aureus | >3.0 × $10^7$ | — | 1.4 × $10^7$ | 2.9 × $10^7$ | 4.3 × $10^7$ | 2.6 × $10^7$ |
| K. pneumoniae + E. gergoviae | >3.0 × $10^7$ | — | 2.4 × $10^7$ | 3.0 × $10^7$ | 3.4 × $10^7$ | 1.7 × $10^7$ |
| P. aeruginosa + B. cepacia | 2.9 × $10^7$ | — | 3.2 × $10^7$ | 2.3 × $10^7$ | 2.0 × $10^7$ | 3.0 × $10^7$ |
| C. albicans | 1.2 × $10^{6*}$ (>3.0 × $10^7$) | — | 1.3 × $10^7$ | 7.0 × $10^5$ (9.9 × $10^6$) | 4.3 × $10^5$ (6.9 × $10^6$) | 3.1 × $10^5$ (>3.0 × $10^6$) |
| Mixed Mold | 1.2 × $10^{4*}$ (>3.0 × $10^7$) | 1.7 × $10^{4*}$ (2.0 × $10^7$) | 1.8 × $10^{4*}$ (>3.0 $10^5$) | 4.0 × $10^{4*}$ (>3.0 $10^6$) | 1.7 × $10^{4*}$ (>3.0 $10^6$) | 1.0 × $10^{4*}$ (>3.0 $10^6$) |

| | Challenge #2 | | | | | |
|---|---|---|---|---|---|---|
| Organism | 24 Hours | 48 Hours | 1 Week | 2 Weeks | 3 Weeks | 4 Weeks |
| S. aureus | 2.7 × $10^7$ | — | 2.1 × $10^7$ | 3.3 × $10^7$ | 2.4 × $10^7$ | 2.7 × $10^7$ |
| K. pneumoniae + E. gergoviae | 2.1 × $10^7$ | — | 1.4 × $10^7$ | 2.7 × $10^7$ | 2.2 × $10^7$ | 1.4 × $10^7$ |
| P. aeruginosa + B. cepacia | 2.0 × $10^7$ | — | 2.0 × $10^7$ | 3.8 × $10^7$ | 3.0 × $10^7$ | 3.7 × $10^7$ |
| C. albicans | 4.8 × $10^5$ (>3.0 $10^6$) | — | 5.0 × $10^5$ (>3.0 $10^6$) | 2.6 × $10^5$ (>3.0 $10^6$) | 2.2 × $10^5$ (>3.0 $10^6$) | 2.9 × $10^5$ (>3.0 $10^6$) |
| Mixed Mold | 3.0 × $10^{4*}$ (>3.0 $10^6$) | 3.1 × $10^{4*}$ (>3.0 $10^6$) | 2.4 × $10^{4*}$ (>3.0 $10^6$) | 1.1 × $10^{5*}$ (>3.0 $10^6$) | 3.1 × $10^{4*}$ (>3.0 $10^6$) | 1.1 × $10^{5*}$ (>3.0 $10^6$) |

\* Bacterial Contamination

TABLE 29b

Lotion with 0.6% ECT 4- Colony Forming Units per Gram (CFU/g)

| | Challenge #1 | | | | | | Challenge #2 | | | | | |
|---|---|---|---|---|---|---|---|---|---|---|---|---|
| Organism | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | <10 | — | <10 | <10 | <10 | <10 | <10 | — | <10 | <10 | <10 | <10 |
| K. pneumoniae + E. gergoviae | <10 | — | <10 | <10 | <10 | <10 | <10 | — | <10 | <10 | <10 | <10 |
| P. aeruginosa + B. cepacia | <10 | — | <10 | <10 | <10 | <10 | <10 | — | <10 | <10 | <10 | <10 |
| C. albicans | <10 | — | <10 | <10 | <10 | <10 | <10 | — | <10 | <10 | <10 | <10 |
| Mixed Mold | 2.0 × $10^1$ | <10 | <10 | <10 | <10 | <10 | 1.4 × $10^2$ | <10 | <10 | <10 | <10 | <10 |

(i) Water in Oil Emulsion, pH N/A, AR12-068 (Data Shown in Tables 30 Through 32b)

Although *S. aureus, K. pneumoniae/E. gergoviae,* and *Ps. aeruginosa/B. cepacia* inocula died off within one week in the unpreserved sample following the first challenge, all the challenge organisms in the preserved samples were reduced to <10 cfu/g within 48 hours. Formulation met CTFA recommendations.

TABLE 30

Inoculum - Colony Forming Units Added per Gram (CFU/g) of Product

| Organism | Challenge #1 CFU/g | Challenge #2 CFU/g |
|---|---|---|
| S. aureus | 1.5 × $10^6$ | 1.6 × $10^6$ |
| K. pneumoniae + E. gergoviae | 1.7 × $10^6$ | 1.6 × $10^6$ |
| P. aeruginosa + B. cepacia | 2.3 × $10^6$ | 2.6 × $10^6$ |
| C. albicans | 5.2 × $10^4$ | 7.1 × $10^4$ |
| Mixed Mold | 1.9 × $10^4$ | 3.9 × $10^4$ |

TABLE 31

Inoculum Recovered from Unpreserved Water in Oil Emulsion (68A) at '0' Hour - Colony Forming Units per Gram (CFU/g)

| Organism | Challenge #1 CFU/g | Challenge #2 CFU/g |
|---|---|---|
| S. aureus | 4.2 × $10^5$ | 1.5 × $10^5$ |
| K. pneumoniae + E. gergoviae | 5.5 × $10^5$ | 2.4 × $10^5$ |

TABLE 31-continued

Inoculum Recovered from Unpreserved Water in Oil Emulsion (68A) at '0' Hour - Colony Forming Units per Gram (CFU/g)

| Organism | Challenge #1 CFU/g | Challenge #2 CFU/g |
|---|---|---|
| P. aeruginosa + B. cepacia | $1.2 \times 10^5$ | $1.2 \times 10^5$ |
| C. albicans | $4.0 \times 10^4$ | $1.2 \times 10^4$ |
| Mixed Mold | $1.7 \times 10^4$ | $3.9 \times 10^4$ |

TABLE 32a

Unpreserved Water in Oil Emulsion - Colony Forming Units per Gram (CFU/g)

| | Challenge #1 | | | | | |
|---|---|---|---|---|---|---|
| Organism | 24 Hours | 48 Hours | 1 Week | 2 Weeks | 3 Weeks | 4 Weeks |
| S. aureus | $7.0 \times 10^4$ | — | <10 | <10 | <10 | <10 |
| K. pneumoniae + E. gergoviae | $1.0 \times 10^1$ | — | <10 | <10 | <10 | <10 |
| P. aeruginosa + B. cepacia | <10 | — | <10 | <10 | <10 | <10 |
| C. albicans | $8.0 \times 10^2$ | — | $1.8 \times 10^2$ | $2.7 \times 10^2$ | $2.1 \times 10^2$ | $3.2 \times 10^2$ |
| Mixed Mold | $2.8 \times 10^3$ | $2.9 \times 10^3$ | $1.8 \times 10^4$ | $1.9 \times 10^4$ | $5.1 \times 10^2$ | $1.1 \times 10^3$ |

| | Challenge #2 | | | | | |
|---|---|---|---|---|---|---|
| Organism | 24 Hours | 48 Hours | 1 Week | 2 Weeks | 3 Weeks | 4 Weeks |
| S. aureus | $2.4 \times 10^5$ | — | <10 | <10 | <10 | <10 |
| K. pneumoniae + E. gergoviae | $8.0 \times 10^1$ | — | <10 | <10 | <10 | <10 |
| P. aeruginosa + B. cepacia | $6.0 \times 10^1$ | — | <10 | $4.0 \times 10^1$ | <10 | <10 |
| C. albicans | $1.0 \times 10^4$ | — | $8.5 \times 10^3$ | $5.4 \times 10^3$ | $6.9 \times 10^3$ | $6.6 \times 10^3$ |
| Mixed Mold | $2.2 \times 10^4$ | $2.7 \times 10^4$ | $2.0 \times 10^4$ | $2.3 \times 10^4$ | $2.8 \times 10^4$ | $1.9 \times 10^4$ |

TABLE 32b

Water in Oil Emulsion with 0.6% ECT 4 - Colony Forming Units per Gram (CFU/g)

| | Challenge #1 | | | | | | Challenge #2 | | | | | |
|---|---|---|---|---|---|---|---|---|---|---|---|---|
| Organism | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | <10 | — | <10 | <10 | <10 | <10 | <10 | — | <10 | <10 | <10 | <10 |
| K. pneumoniae + E. gergoviae | <10 | — | <10 | <10 | <10 | <10 | <10 | — | <10 | <10 | <10 | <10 |
| P. aeruginosa + B. cepacia | <10 | — | <10 | <10 | <10 | <10 | <10 | — | <10 | <10 | <10 | <10 |
| C. albicans | <10 | — | <10 | <10 | <10 | <10 | <10 | — | <10 | <10 | <10 | <10 |
| Mixed Mold | $7.0 \times 10^1$ | <10 | <10 | <10 | <10 | <10 | <10 | <10 | <10 | <10 | <10 | <10 |

TABLE 33

Inoculum - Colony Forming Units Added per Gram (CFU/g) of Make-up Remover, pH 8.1 (45A-C)

| Organism | Challenge #1 CFU/g | Challenge #2 CFU/g |
|---|---|---|
| S. aureus | $1.5 \times 10^6$ | — |
| K. pneumoniae + E. gergoviae | $1.7 \times 10^6$ | — |
| P. aeruginosa + B. cepacia | $2.3 \times 10^6$ | — |
| C. albicans | $5.2 \times 10^4$ | — |
| Mixed Mold | $1.9 \times 10^4$ | — |

(i) Make-Up Remover, pH 8.1, KKL 14-45 (Data Shown in Tables 33 Through 35b)

This formulation with 0.6% ECT 4 did not meet the CTFA recommendations for a 90% decrease in fungi within 1 week. The unpreserved samples had very little survival of the Staph, Klebsiella, Pseudomonas and Enterobacter; but the Pseudomonas, Burkholderia, yeast and fungi did survive. Formulation did not meet CTFA recommendations, whereas a 1% dose gave good activity (see Table 20b). Testing was discontinued before the second challenge was to be done due to failure of product.

TABLE 34

Inoculum Recovered from Make-up Remover, pH 8.1 (45A) at '0' Hour - Colony Forming Units per Gram (CFU/g)

| Organism | Challenge #1 CFU/g | Challenge #2 CFU/g |
|---|---|---|
| S. aureus | $6.1 \times 10^3$ | — |
| K. pneumoniae + E. gergoviae | $4.7 \times 10^5$ | — |
| P. aeruginosa + B. cepacia | $5.2 \times 10^2$ | — |
| C. albicans | $1.2 \times 10^4$ | — |
| Mixed Mold | $6.5 \times 10^4$ | — |

TABLE 36

Inoculum - Colony Forming Units Added per Gram (CFU/g) of Product

| Organism | Challenge #1 | Challenge #2 |
|---|---|---|
| S. aureus | $2.5 \times 10^6$ | $2.0 \times 10^6$ |
| P. aeruginosa + B. cepacia | $3.7 \times 10^6$ | $3.0 \times 10^6$ |
| K. pneumoniae + E. gergoviae | $1.8 \times 10^6$ | $3.0 \times 10^6$ |
| C. albicans | $1.3 \times 10^5$ | $1.6 \times 10^5$ |
| Mixed Molds | $1.1 \times 10^5$ | $2.2 \times 10^4$ |

TABLE 35a

Unpreserved Make-up Remover, pH 8.1 - Colony Forming Units per Gram (CFU/g)

| Organism | Challenge #1 | | | | | | Challenge #2 | | | | | |
|---|---|---|---|---|---|---|---|---|---|---|---|---|
| | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | <10 | — | <10 | <10 | <10 | <10 | Test terminated | | | | | |
| K. pneumoniae + E. gergoviae | $4.0 \times 10^1$ | — | <10 | <10 | <10 | <10 | | | | | | |
| P. aeruginosa + B. cepacia | <10 | — | lawn | lawn | $4.3 \times 10^6$ | $2.5 \times 10^6$ | | | | | | |
| C. albicans | $8.1 \times 10^2$ | — | $2.6 \times 10^2$ | $2.0 \times 10^1$ | <10 | <10 | | | | | | |
| Mixed Mold | $4.7 \times 10^4$ | $4.1 \times 10^4$ | $4.7 \times 10^4$ | $2.0 \times 10^4$ | $1.9 \times 10^4$ | $6.3 \times 10^3$ | | | | | | |

TABLE 35b

Make-up Remover, pH 8.1 with 0.6% ECT 4 - Colony Forming Units per Gram (CFU/g)

| Organism | Challenge #1 | | | | | | Challenge #2 | | | | | |
|---|---|---|---|---|---|---|---|---|---|---|---|---|
| | 24 Hours | 48 Hours | 1 Week | 2 Weeks | 3 Weeks | 4 Weeks | 24 Hours | 48 Hours | 1 Week | 2 Weeks | 3 Weeks | 4 Weeks |
| S. aureus | <10 | — | <10 | <10 | — | <10 | Test terminated | | | | | |
| K. pneumoniae + E. gergoviae | $3.0 \times 10^1$ | — | <10 | <10 | — | <10 | | | | | | |
| P. aeruginosa + B. cepacia | <10 | — | <10 | <10 | — | <10 | | | | | | |
| C. albicans | $1.4 \times 10^3$ | — | $4.0 \times 10^1$ | <10 | — | <10 | | | | | | |
| Mixed Mold | $2.1 \times 10^4$ | $4.2 \times 10^4$ | $1.5 \times 10^4$ | $1.5 \times 10^4$ | — | $4.0 \times 10^3$ | | | | | | |

To determine if the unexpected activity of ECT 4 at high pH (8.1) can be attributed solely to the activity of benzyl alcohol the high pH make-up remover was preserved with 1% ECT4 and with 0.83% benzyl alcohol (equivalent amount found in 1% ECT4).

Summary of Results:

The data shows that ECT4 is more effective than its benzyl alcohol alone, Tables 39 and 40 show that benzyl alcohol alone was not sufficiently efficacious against the mixed mold challenge. High pH Make-up Remover preserved only with benzyl alcohol did not meet CTFA recommendations for a minimum of 90% mold reduction in 7 days; the sample with 1% ECT4 does meet this criterion. This is unexpected as the organic acids in ECT4 would not be expected to have any activity at this high a pH.

TABLE 37

Inoculum Recovered from unpreserved product at '0' Hour - Colony Forming Units per Gram (CFU/g)

| Organism | Challenge #1 CFU/g | Challenge #2 CFU/g |
|---|---|---|
| S. aureus | $5.5 \times 10^4$ | NP |
| P. aeruginosa + B. cepacia | $2.3 \times 10^5$ | NP |
| K. pneumoniae + E. gergoviae | $3.7 \times 10^5$ | NP |
| C. albicans | $7.4 \times 10^5$ | NP |
| Mixed molds | $9.0 \times 10^4$ | NP |

NP = Not Plated, contaminant overgrew challenge bacteria

TABLE 38

Unpreserved - Colony Forming Units per Gram (CFU/g)

| Test Organism | Challenge # 1 | | | | | | Challenge # 2 | | | | | |
|---|---|---|---|---|---|---|---|---|---|---|---|---|
| | 24 Hours | 48 Hours | 7 Days | 14 Days | 21 Days | 28 Days | 24 Hours | 48 Hours | 7 Days | 14 Days | 21 Days | 28 Days |
| S. aureus | $3.7 \times 10^4$ | — | * | * | NP | NP | NP | — | NP | NP | NP | NP |
| P. aeruginosa + B. cepacia | $6.7 \times 10^4$ | — | * | * | NP | NP | NP | — | NP | NP | NP | NP |
| K. pneumoniae + E. gergoviae | $4.0 \times 10^5$ | — | * | * | NP | NP | NP | — | NP | NP | NP | NP |
| C. albicans | $2.7 \times 10^5$ | — | * | * | NP | NP | NP | — | NP | NP | NP | NP |
| Mixed Molds | $8.0 \times 10^4$ | $2.0 \times 10^5$ | * | * | NP | NP | NP | NP | NP | NP | NP | NP |

\* Contaminant overgrew challenge bacteria

NP = Not Plated, contaminant overgrew challenge bacteria

TABLE 39

Make-up Remover with 1% ECT 4- Colony Forming Units per Gram (CFU/g)

| Test Organism | Challenge # 1 | | | | | |
|---|---|---|---|---|---|---|
| | 24 Hours | 48 Hours | 7 Days | 14 Days | 21 Days | 28 Days |
| S. aureus | <10 | — | <10 | <10 | <10 | <10 |
| P. aeruginosa + B. cepacia | <10 | — | <10 | <10 | <10 | <10 |
| K. pneumoniae + E. gergoviae | $2.1 \times 10^3$ | — | <10 | <10 | <10 | <10 |
| C. albicans | $1.8 \times 10^5$ | — | <10 | <10 | <10 | <10 |
| Mixed Molds | $5.0 \times 10^4$ | $5.0 \times 10^4$ | $3.0 \times 10^3$ | $4.2 \times 10^2$ | $2.8 \times 10^2$ | $2.1 \times 10^2$ |

| Test Organism | Challenge #2 | | | | | |
|---|---|---|---|---|---|---|
| | 24 Hours | 48 Hours | 7 Days | 14 Days | 21 Days | 28 Days |
| S. aureus | NP | <10 | <10 | <10 | <10 | <10 |
| P. aeruginosa + B. cepacia | NP | <10 | <10 | <10 | <10 | <10 |
| K. pneumoniae + E. gergoviae | NP | <10 | <10 | <10 | <10 | <10 |
| C. albicans | NP | $<1.0 \times 10^2$ | <10 | <10 | <10 | <10 |
| Mixed Molds | NP | $1.0 \times 10^2$ | $3.0 \times 10^1$ | $6.0 \times 10^1$ | $1.0 \times 10^1$ | <10 |

NP = Not plated

TABLE 40

Make-up Remover at pH 8.1 with 0.83% Benzyl Alcohol - Colony Forming Units per Gram (CFU/g)

| Test Organism | Challenge # 1 | | | | | |
|---|---|---|---|---|---|---|
| | 24 Hours | 48 Hours | 7 Days | 14 Days | 21 Days | 28 Days |
| S. aureus | <10 | — | <10 | <10 | <10 | <10 |
| P. aeruginosa + B. cepacia | <10 | — | <10 | <10 | <10 | <10 |
| K. pneumoniae + E. gergoviae | <10 | — | <10 | <10 | <10 | <10 |
| C. albicans | $3.1 \times 10^4$ | — | $1.6 \times 10^2$ | <10 | <10 | <10 |
| Mixed Molds | $2.1 \times 10^5$ | $1.2 \times 10^5$ | $3.0 \times 10^4$ | $8.0 \times 10^4$ | $1.5 \times 10^4$ | $5.1 \times 10^3$ |

| Test Organism | Challenge # 2 | | | | | |
|---|---|---|---|---|---|---|
| | 24 Hours | 48 Hours | 7 Days | 14 Days | 21 Days | 28 Days |
| S. aureus | NP | <10 | <10 | <10 | <10 | <10 |
| P. aeruginosa + B. cepacia | NP | <10 | <10 | <10 | <10 | <10 |

TABLE 40-continued

Make-up Remover at pH 8.1 with 0.83% Benzyl Alcohol -
Colony Forming Units per Gram (CFU/g)

| | | | | | | |
|---|---|---|---|---|---|---|
| K. pneumoniae + E. gergoviae | NP | <10 | <10 | <10 | <10 | <10 |
| C. albicans | NP | <1.0 × 10$^2$ | <10 | <10 | <10 | <10 |
| Mixed Molds | NP | 3.8 × 10$^3$ | 3.4 × 10$^3$ | 3.6 × 10$^3$ | 9.0 × 10$^3$ | 4.0 × 10$^2$ |

NP = Not plated

While the invention has been described above with reference to specific embodiments thereof, it is apparent that many changes, modifications, and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A composition having effective broad spectrum preservation activity comprising: (a) benzyl alcohol, (b) salicylic acid, (c) sorbic acid and (d) a compound selected from the group consisting of 1,3-propanediol, glycerin and a combination thereof, wherein component (a) is present at a concentration of from about 70% to about 90% by weight, component (b) is present at a concentration of from about 1% to 15% by weight, component (c) is present at a concentration of from about 1% to 4% by weight, and component (d) is present at a concentration of from about 1% to 15% by weight, provided that the total amount of components (b) and (c) is no more than 15% by weight, all based on the total weight of the composition.

2. The composition of claim 1, further comprising water in an amount less than 1000 parts per million.

3. The composition of claim 1, wherein the total weight percentage of component (a), (b), (c) and (d) combined is 100%.

4. The composition of claim 1, wherein component (a) is present at a concentration of from about 77% to 86% by weight, component (b) is present at a concentration of from about 3% to about 12% by weight, component (c) is present at a concentration of from about 2.5% to 3.5% by weight, and component (d) is present at a concentration of from about 1% to 10% by weight, based on the total weight of the composition.

5. The composition of claim 1, wherein component (d) is glycerin present at a concentration of from about 2% to about 5%.

6. The composition of claim 1 wherein component (d) is 1,3-propanediol presented at a concentration of from about 2% to about 5%.

7. The composition of claim 1, further comprising dehydroacetic acid, wherein the total amount of salicylic acid, sorbic acid, and dehydroacetic acid is no more than 15 wt % of the composition.

8. The composition of claim 7, wherein the dehydroacetic acid and the component (d) are present at a weight ratio range of from about 3:1 to 1:1.

9. The composition of claim 1, wherein component (a) is present at a concentration of from about 77% to about 86%, component (b) is present at a concentration of from about 8% to 11%, component (c) is present at concentration of from about 2.5% to 3.5%, and component (d) is glycerin present at a concentration of from about 2% to about 5%, all based on the weight of the composition.

10. A topical formulation comprising the preservative composition of claim 1 and additives selected from the group consisting of solvents, surfactants, emulsifiers, consistency factors, conditioners, emollients, skin caring ingredients, moisturizers, thickeners, lubricants, fillers, anti-oxidants, other preservatives, active ingredients, fragrances and mixtures thereof.

11. The topical formulation of claim 10, wherein the preservative composition is present at a concentration of from about 0.5% to about 1.5% based on the weight of the formulation.

12. The topical formulation of claim 11, wherein the preservative composition is present at a concentration of from about 0.6% to about 1% based on the weight of the formulation.

13. The topical formulation of claim 10, wherein the formulation is in the form of an oil-in-water emulsion.

14. The topical formulation of claim 10 wherein the formulation is in the form of a water-in-oil emulsion.

15. A composition having effective broad spectrum preservation activity consisting of: (a) benzyl alcohol, (b) salicylic acid, (c) sorbic acid and (d) a compound selected from the group consisting of 1,3-propanediol, glycerin and a combination thereof; and (e) optionally, dehydroacetic acid, wherein component (a) is present at a concentration of from about 70% to about 90% by weight, component (b) is present at a concentration of from about 1% to 15% by weight, component (c) is present at a concentration of from about 1% to 4% by weight, and component (d) is present at a concentration of from about 1% to 15% by weight, and wherein total amount of components (b), (c) and (a) is no more than 15% by weight, all based on the total weight of the composition.

16. The composition of claim 15, wherein component (a) is present at a concentration of from about 77% to 86% by weight, component (b) is present at a concentration of from about 3% to about 12% by weight, component (c) is present at a concentration of from about 2.5% to 3.5% by weight, and component (d) is present at a concentration of from about 1% to 10% by weight, based on the total weight of the composition.

17. The composition of claim 15, further comprising dehydroacetic acid, wherein the total amount of salicylic acid, sorbic acid, and dehydroacetic acid is no more than 15 wt % of the composition.

18. A topical formulation comprising the preservative composition of claim 15 and additives selected from the group consisting of solvents, surfactants, emulsifiers, consistency factors, conditioners, emollients, skin caring ingredients, moisturizers, thickeners, lubricants, fillers, anti-oxidants, other preservatives, active ingredients, fragrances and mixtures thereof.

19. The topical formulation of claim 18, wherein the preservative composition is present at a concentration of from about 0.5% to about 1.5% based on the weight of the formulation.

20. A composition having effective broad spectrum preservation activity comprising: (a) benzyl alcohol, (b) salicylic acid, (c) sorbic acid, (d) a compound selected from the group consisting of 1,3-propanediol, glycerin and a combination thereof, and (e) dehydroacetic acid, wherein component (a) is present at a concentration of from about 70% to about 90% by weight, component (b) is present at a concentration of from about 1% to 15% by weight, component (c) is present at a concentration of from about 1% to 4% by weight, and component (d) is present at a concentration of from about 1% to 15% by weight, provided that the total amount of components (b), (c), and (e) is no more than 15% by weight, all based on the total weight of the composition, and wherein water is present in an amount of less than 1000 parts per million.

21. The composition of claim 1, wherein the composition has a pH of greater than 7.

22. The composition of claim 15, wherein the composition has a pH of greater than 7.

* * * * *